(12) United States Patent
Qian et al.

(10) Patent No.: US 12,180,184 B2
(45) Date of Patent: Dec. 31, 2024

(54) PYRIMIDOPYRAZOLONE DERIVATIVE AS WEE1 INHIBITOR AND USE THEREOF

(71) Applicant: Wuxi Biocity Biopharmaceutics Co., Ltd., Wuxi Jiangsu (CN)

(72) Inventors: Wenyuan Qian, Shanghai (CN); Chundao Yang, Shanghai (CN); Zhengwei Li, Shanghai (CN); Jian Li, Shanghai (CN); Shuhui Chen, Shanghai (CN)

(73) Assignee: Wuxi Biocity Biopharmaceutics Co., Ltd., Wuxi Jiangsu (CN)

( * ) Notice: Subject to any disclaimer, the term of this patent is extended or adjusted under 35 U.S.C. 154(b) by 0 days.

(21) Appl. No.: 17/288,707

(22) PCT Filed: Oct. 28, 2019

(86) PCT No.: PCT/CN2019/113622
§ 371 (c)(1),
(2) Date: Apr. 26, 2021

(87) PCT Pub. No.: WO2020/083404
PCT Pub. Date: Apr. 30, 2020

(65) Prior Publication Data
US 2021/0403451 A1  Dec. 30, 2021

(30) Foreign Application Priority Data

Oct. 26, 2018  (CN) .......................... 201811257877.3
Jul. 18, 2019   (CN) .......................... 201910650345.4

(51) Int. Cl.
| C07D 401/14 | (2006.01) |
|---|---|
| A61P 35/00 | (2006.01) |
| A61K 31/519 | (2006.01) |
| A61K 31/7068 | (2006.01) |
| C07D 487/22 | (2006.01) |

(52) U.S. Cl.
CPC ............ *C07D 401/14* (2013.01); *A61P 35/00* (2018.01)

(58) Field of Classification Search
CPC ...... C07D 401/14; C07D 487/22; A61P 35/00; A61K 31/7068; A61K 31/519
See application file for complete search history.

(56) References Cited

U.S. PATENT DOCUMENTS

| 11,613,545 B2 * | 3/2023 | Qian .................... C07D 519/00 514/218 |
|---|---|---|
| 2007/0254892 A1 | 11/2007 | Sagara et al. |
| 2010/0063024 A1 | 3/2010 | Sakamoto et al. |
| 2012/0220572 A1 | 6/2012 | Laboratories |
| 2020/0325145 A1 | 10/2020 | Shijiazhuang |
| 2020/0377520 A1 | 12/2020 | Shanghai |

FOREIGN PATENT DOCUMENTS

| CN | 101432284 A | 5/2009 |
|---|---|---|
| EP | 2213673 A1 | 4/2010 |
| JP | 2012511502 A | 5/2012 |
| JP | 2016520645 A | 7/2016 |
| WO | 2007126122 A1 | 11/2007 |
| WO | 2008133866 A1 | 11/2008 |
| WO | 2010067886 A1 | 6/2010 |
| WO | 2011034743 A1 | 3/2011 |
| WO | 2013012681 A1 | 1/2013 |
| WO | 2013013031 A1 | 1/2013 |
| WO | 2013059485 A1 | 4/2013 |
| WO | 2013126656 A1 | 8/2013 |
| WO | 2014167347 A1 | 10/2014 |
| WO | 2014195919 A1 | 11/2014 |
| WO | 2015019037 A1 | 2/2015 |
| WO | 2015092431 A1 | 6/2015 |
| WO | 2017075629 A2 | 5/2017 |
| WO | 2018171633 A1 | 9/2018 |
| WO | 2019085933 A1 | 5/2019 |

OTHER PUBLICATIONS

Gleeson MP, Hersey A, Montanari D, Overington J. Probing the links between in vitro potency, ADMET and physicochemical parameters. Nat Rev Drug Discov. Mar. 2011;10(3):197-208. doi: 10.1038/nrd3367. PMID: 21358739; PMCID: PMC6317702. (Year: 2011).*

Rao CV, Asch AS, Carr DJJ, Yamada HY. "Amyloid-beta accumulation cycle" as a prevention and/or therapy target for Alzheimer's disease. Aging Cell. Mar. 2020;19(3):e13109. doi: 10.1111/acel.13109. Epub Jan. 25, 2020. PMID: 31981470; PMCID: PMC7059149. (Year: 2020).*

Organic Chemistry of Drug Design and Action, 2nd Ed, 2004 (Year: 2004).*

Esposito F, Giuffrida R, Raciti G, Puglisi C, Forte S. Wee1 Kinase: A Potential Target to Overcome Tumor Resistance to Therapy. Int J Mol Sci. Oct. 1, 2021;22(19):10689. doi: 10.3390/ijms221910689. PMID: 34639030; PMCID: PMC8508993. (Year: 2021).*

(Continued)

Primary Examiner — Bruck Kifle
Assistant Examiner — Kevin S Martin
(74) Attorney, Agent, or Firm — Ice Miller LLP

(57) ABSTRACT

A pyrimidopyrazolone derivative as a Wee1 inhibitor and use thereof in preparation of a medicament for treating Wee1-related diseases are described. In particular, the present invention relates to a compound of formula (I), an isomer or a pharmaceutically acceptable salt thereof.

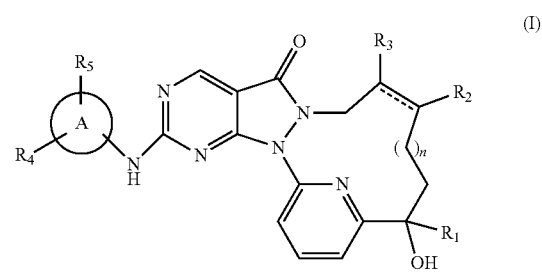

22 Claims, No Drawings
Specification includes a Sequence Listing.

(56) References Cited

OTHER PUBLICATIONS

Cecil Textbook of Medicine, 20th Ed, vol. 1, 1997 (Year: 1997).*
Wu Q, Qian W, Sun X, Jiang S. Small-molecule inhibitors, immune checkpoint inhibitors, and more: FDA-approved novel therapeutic drugs for solid tumors from 1991 to 2021. J Hematol Oncol. Oct. 8, 2022;15(1):143. doi: 10.1186/s13045-022-01362-9. PMID: 36209184; PMCID: PMC9548212. (Year: 2022).*
International Search Report issued Feb. 3, 2020 in PCT/CN2019/113622.
Written Opinion issued Feb. 3, 2020 in PCT/CN2019/113622.
Japanese Office Action issued Nov. 20, 2023 in corresponding JP application No. 2021-522414.

* cited by examiner

SEQUENCE LISTING

```
<160> NUMBER OF SEQ ID NOS: 1

<210> SEQ ID NO 1
<211> LENGTH: 23
<212> TYPE: PRT
<213> ORGANISM: Artificial Sequence
<220> FEATURE:
<223> OTHER INFORMATION: polypeptide substrate

<400> SEQUENCE: 1

Leu Ser Asn Leu Tyr His Gln Gly Lys Phe Leu Gln Thr Phe Cys Gly
1               5                   10                  15

Ser Pro Leu Tyr Arg Arg Arg
            20
```

PYRIMIDOPYRAZOLONE DERIVATIVE AS WEE1 INHIBITOR AND USE THEREOF

CROSS REFERENCE TO RELATED APPLICATIONS

The present application is a Section 371 of International Application No. PCT/CN2019/113622 filed Oct. 28, 2019, which was published in the Chinese language Apr. 30, 2020 under International Publication No. WO 2020/083404, which claims priority to Chinese Application No. 201811257877.3 filed on Oct. 26, 2018 and Chinese Application No. 201910650345.4 filed on Jul. 28, 2019, the disclosures of which are incorporated herein by reference in their entireties.

REFERENCE TO SEQUENCE LISTING SUBMITTED ELECTRONICALLY

This application contains a sequence listing, which is submitted electronically via EFS-Web as an ASCII formatted sequence listing with a file name of "NP2021TC741US01_ST25" creation date of Jan. 12, 2024, and having a size of 1 KB. The sequence listing submitted via EFS-Web is part of the specification and is herein incorporated by reference in its entirety.

TECHNICAL FIELD

Provided is a pyrimidopyrazolone derivative as Wee1 inhibitor and the use for the manufacture of a medicament for treating a Wee1 associated disease. Specifically, provided is a compound of formula (I), or an isomer or a pharmaceutically acceptable salt thereof.

BACKGROUND

The cell cycle process is a complex process under the control of a series of cell cycle regulatory systems. The key of the cell cycle regulatory system is CDKs/Cyclins complex formed by the combination of cyclin-dependent kinases (CDKs) and cyclins (Cyclins). The complex can drive cells to enter the proliferation cycle, wherein the CDK1 (the human autoploid is also known as CDC2)/Cyclin B complex plays a key role in controlling cells into the M phase.

The DNA replication has to be completed before the cell enters the M phase. Due to the interference of various endogenous and exogenous factors, the mutations or damages often occur to the DNA. The abnormal DNA must be repaired, or it will cause mitotic disaster and cause cell death. The cell cycle checkpoint will cease the cell cycle and allow the repair of DNA before its entry of the M phase. The G1/S checkpoint at the end of the G1 phase and the G2/M checkpoint at the G2 phase are two main cell cycle checkpoints, which together are responsible for the recognition and repair of DNA damage. Normal cells utilize the G1/S checkpoint to complete DNA repair in the G1 phase, while nearly 50% of cancerous cells have defects in the tumor suppressor gene p53, rendering them lacking the G1/S checkpoint function. They have to rely more on the G2/M checkpoint to complete DNA repair. The G2/M checkpoint rarely undergoes mutations, making the cancer cells escape the treatment of DNA damaging agents and radiation.

Wee1 protein kinase is a cell cycle regulator, a member of the serine and threonine protein kinase family in the nucleus and is a key kinase for the G2/M checkpoint. The human "Wee" protein kinase family mainly includes Wee1 and Myt1, both of which can phosphorylate the Tyr15 site on CDC2, inhibit the activation of the CDC2/CyclinB complex, and block cells from entering the M phase until the DNA repair is completed. Myt1 can also phosphorylate the Thr14 site on CDC2, which is also a negative regulation of CDC2 activity. Wee1 kinase is highly expressed in many cancerous cells. By inhibiting Wee1 kinase, the tumor cells can be directly made to skip the DNA repair of G2 stage and enter mitosis in advance, which leads to tumor cell death, and achieve the purpose of treating cancer.

At present, a Wee1 inhibitor AZD1775 by AstraZeneca has entered the clinical phase II, and more than 30 clinical trials are under development, showing good therapeutic effects. AZD1775 was first developed by Merck, and therefore it is also known as MK-1775. In September 2013, Merck transferred the compound to AstraZeneca globally, and the relevant patents mainly include US20070254892, WO2007126122, EP2213673, WO2008133866, WO2011034743, etc. Abbott and Abbvie have also conducted research on Wee1 inhibitors, and relevant patents mainly include US2012220572, WO2013126656, WO2013012681, WO2013059485, WO2013013031, WO2013126656, etc. Almac's patents regarding Wee1 inhibitors include WO2014167347, WO2015019037, WO2015092431.

SUMMARY

Provided is a compound of formula (I), or an isomer or a pharmaceutically acceptable salt thereof,

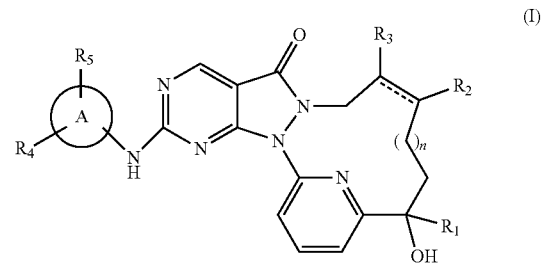

wherein

⩘ is a single bond or a double bond;

n is 1, 2 or 3;

ring A is selected from the group consisting of $C_{6-10}$ aryl, 5-12 membered heteroaryl, $C_{3-8}$ cycloalkyl and 4-10 membered heterocycloalkyl;

$R_1$ is selected from the group consisting of H and $C_{1-3}$ alkyl, wherein the $C_{1-3}$ alkyl is optionally substituted by 1, 2 or 3 $R_a$;

$R_2$ and $R_3$ are each independently selected from the group consisting of H, F, Cl, Br, I, OH, $NH_2$ and $C_{1-3}$ alkyl, wherein the $C_{1-3}$ alkyl is optionally substituted by 1, 2 or 3 $R_b$, and $R_2$ and $R_3$ are not H at the same time;

$R_4$ is selected from the group consisting of $C_{3-8}$ cycloalkyl and 4-10 membered heterocycloalkyl, wherein the $C_{3-8}$ cycloalkyl and 4-10 membered heterocycloalkyl are optionally substituted by 1, 2 or 3 $R_c$;

$R_5$ is selected from the group consisting of H, F, Cl, Br, I, OH, $NH_2$, $C_{1-3}$ alkyl and $C_{1-3}$ alkoxy, wherein the $C_{1-3}$ alkyl is optionally substituted by 1, 2 or 3 $R_d$;

$R_a$ is each independently selected from the group consisting of F, Cl, Br, I, OH and $NH_2$;

R$_b$ is each independently selected from the group consisting of F, Cl, Br, I, OH and NH$_2$;

R$_c$ is each independently selected from the group consisting of H, F, Cl, Br, I, OH, NH$_2$ and C$_{1-3}$ alkyl, wherein the NH$_2$ and C$_{1-3}$ alkyl are optionally substituted by 1, 2 or 3 R;

R$_d$ is each independently selected from the group consisting of F, Cl, Br, I, OH and NH$_2$;

R is each independently selected from the group consisting of F, Cl, Br, I, OH and NH$_2$;

the 5-12 membered heteroaryl and 4-10 membered heterocycloalkyl contain 1, 2, 3 or 4 heteroatoms or heteroradicals independently selected from the group consisting of —NH—, O, —S— and N.

In some embodiments according to the present disclosure, the ring A is selected from the group consisting of C$_{6-8}$ membered aryl and 5-10 membered heteroaryl, and other variables are defined as herein.

In some embodiments according to the present disclosure, the compound has the structure of formula (II) or (III):

(II)

(III)

wherein,
⤳ is a single bond or a double bond;
n is 1, 2 or 3;

R$_1$ is each independently selected from the group consisting of H and C$_{1-3}$ alkyl, wherein the C$_{1-3}$ alkyl is optionally substituted by 1, 2 or 3 R$_a$;

R$_2$ and R$_3$ are each independently selected from the group consisting of H, F, Cl, Br, I, OH, NH$_2$ and C$_{1-3}$ alkyl, wherein the C$_{1-3}$ alkyl is optionally substituted by 1, 2 or 3 R$_b$, and R$_2$ and R$_3$ are not H at the same time;

R$_4$ is each independently selected from the group consisting of C$_{3-8}$ cycloalkyl and 4-10 membered heterocycloalkyl, wherein the C$_{3-8}$ cycloalkyl and 4-10 membered heterocycloalkyl are optionally substituted by 1, 2 or 3 R$_c$;

R$_5$ is each independently selected from the group consisting of H, F, Cl, Br, I, OH, NH$_2$, C$_{1-3}$ alkyl and C$_{1-3}$ alkoxy, wherein the C$_{1-3}$ alkyl is optionally substituted by 1, 2 or 3 R$_d$;

R$_a$ is each independently selected from the group consisting of F, Cl, Br, I, OH and NH$_2$;

R$_b$ is each independently selected from the group consisting of F, Cl, Br, I, OH and NH$_2$;

R$_c$ is each independently selected from the group consisting of H, F, Cl, Br, I, OH, NH$_2$ and C$_{1-3}$ alkyl, wherein the NH$_2$ and C$_{1-3}$ alkyl are optionally substituted by 1, 2 or 3 R;

R$_d$ is each independently selected from the group consisting of F, Cl, Br, I, OH and NH$_2$;

R is each independently selected from the group consisting of F, Cl, Br, I, OH and NH$_2$;

the 4-10 membered heterocycloalkyl contains 1, 2, 3 or 4 heteroatoms or heteroradicals independently selected from the group consisting of —NH—, O, —S— and N;

the carbon atom with "*" is a chiral carbon atom, which is present in a form of a single enantiomer as (R) or (S) or in a form enriched with an enantiomer.

In some embodiments according to the present disclosure, the compound has the structure of formula (II-A) or (III-A):

(II-A)

(III-A)

wherein,
r is 1 or 2;
D is each independently selected from the group consisting of —N(R$_6$)— and —C(R$_7$)(R$_8$)—;

R$_6$ is each independently selected from the group consisting of H and C$_{1-3}$ alkyl, wherein the C$_{1-3}$ alkyl is optionally substituted by 1, 2 or 3 R$_e$;

R$_7$ and R$_8$ are each independently selected from the group consisting of H, F, Cl, Br, I, OH, NH$_2$ and C$_{1-3}$ alkyl, wherein the NH$_2$ and C$_{1-3}$ alkyl are optionally substituted by 1, 2 or 3 R$_f$;

R$_e$ is each independently selected from the group consisting of F, Cl, Br, I, OH and NH$_2$;

R$_f$ is each independently selected from the group consisting of F, Cl, Br, I, OH, NH$_2$ and C$_{1-3}$ alkyl;

the carbon atom with "*" is a chiral carbon atom, which is present in a form of a single enantiomer as (R) or (S) or in a form enriched with an enantiomer;

R$_1$, R$_2$ and R$_3$ are as defined herein.

In some embodiments according to the present disclosure, the $R_c$ is each independently selected from the group consisting of F, Cl, Br, I, OH, $NH_2$, $CH_3$ and Et, and other variables are defined as herein.

In some embodiments according to the present disclosure, the $R_f$ is each independently selected from the group consisting of F, Cl, Br, I, OH, $NH_2$, $CH_3$ and Et, and other variables are defined as herein.

In some embodiments according to the present disclosure, the $R_1$ is each independently selected from the group consisting of H, $CH_3$ and Et, and other variables are defined as herein.

In some embodiments according to the present disclosure, the $R_2$ and $R_3$ are each independently selected from the group consisting of H, F, Cl, Br, I, OH, $NH_2$, $CH_3$ and Et, and $R_2$ and $R_3$ are not H at the same time, and other variables are defined as herein.

In some embodiments according to the present disclosure, the $R_5$ is each independently selected from the group consisting of H, F, Cl, Br, I, OH, $NH_2$, $CH_3$, Et and $OCH_3$, and other variables are defined as herein.

In some embodiments according to the present disclosure, the $R_6$ is each independently selected from the group consisting of H, $CH_3$ and Et, and other variables are defined as herein.

In some embodiments according to the present disclosure, the $R_7$ and $R_8$ are each independently selected from the group consisting of H, F, Cl, Br, I, OH, $NH_2$, —$NH(CH_3)$, —$N(CH_3)_2$, $CH_3$ and Et, and other variables are defined as herein.

In some embodiments according to the present disclosure, the $R_7$ is each independently selected from the group consisting of H, F, Cl, Br, I, OH, $NH_2$, —$NH(CH_3)$, —$N(CH_3)_2$, $CH_3$ and Et, and other variables are defined as herein.

In some embodiments according to the present disclosure, the $R_8$ is each independently selected from the group consisting of H, F, Cl, Br, I, OH, $CH_3$ and Et, and other variables are defined as herein.

In some embodiments according to the present disclosure, the structural unit

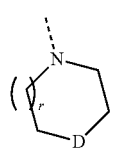

is selected from the group consisting of

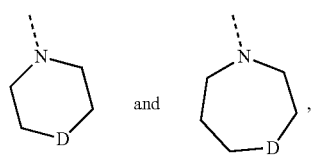

and other variables are defined as herein.

In some embodiments according to the present disclosure, the structural unit

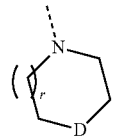

is selected from the group consisting of

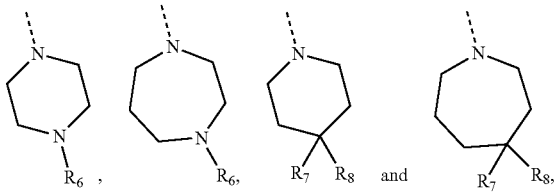

and other variables are defined as herein.

In some embodiments according to the present disclosure, the structural unit

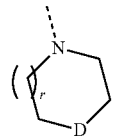

is selected from the group consisting of

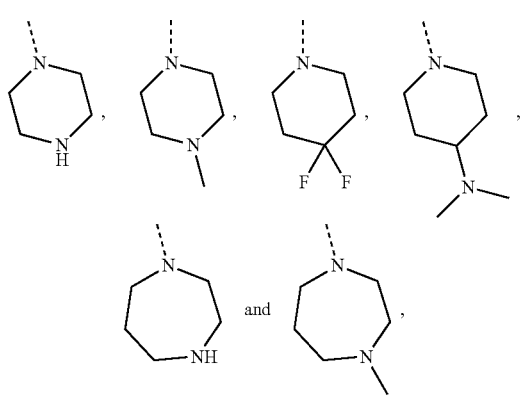

and other variables are defined as herein.

In some embodiments according to the present disclosure, the structural unit

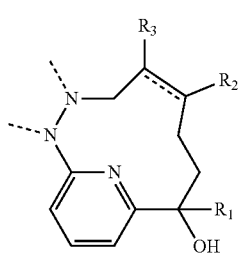

is selected from the group consisting of

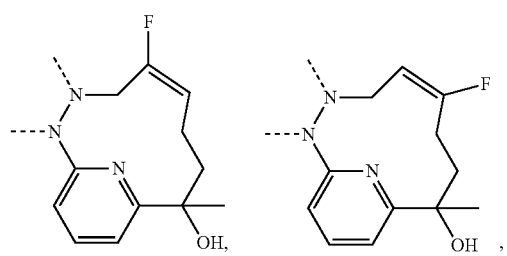

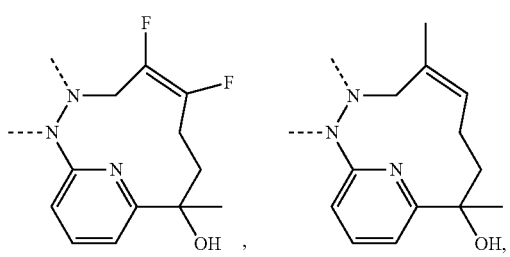

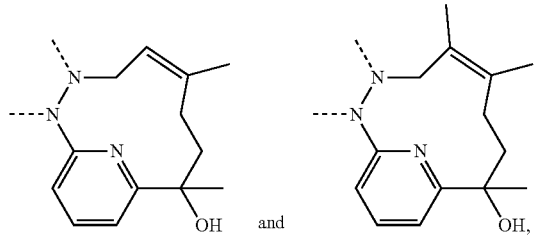

and other variables are defined as herein.

In some embodiments according to the present disclosure, provided is a compound or an enantiomer or an optical isomer or a pharmaceutically acceptable salt thereof, wherein the compound has the structure of formula (II-A1), (II-A2) or (III-AA1)

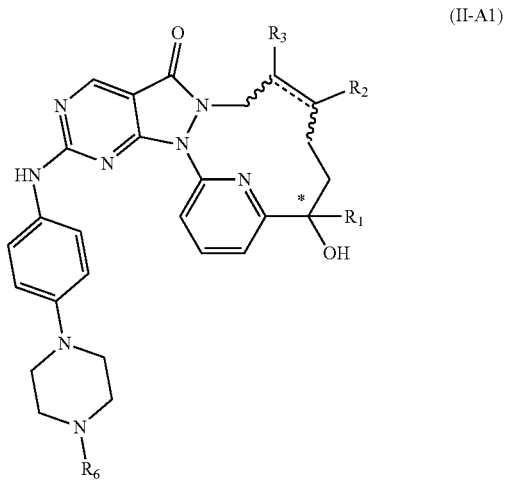
(II-A1)

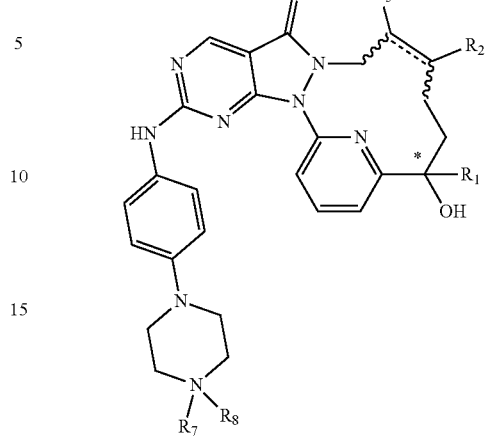
(II-A2)

(III-AA1)

wherein, $R_1$, $R_2$, $R_3$, $R_6$, $R_7$ and $R_8$ are as defined herein;

the carbon atom with "*" is a chiral carbon atom, which is present in a form of a single enantiomer as (R) or (S) or in a form enriched with an enantiomer;

the " ⁓ " refers to (Z) isomer, (E) isomer or a mixture of two isomers of the compound.

In some embodiments according to the present disclosure, provided is a compound or an enantiomer or a pharmaceutically acceptable salt thereof, wherein the compound has the structure of formula (II-1), (II-2) or (III-A1)

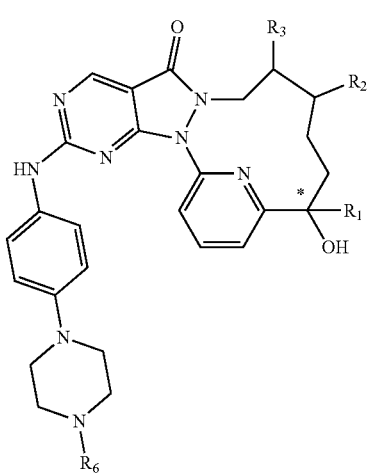
(II-1)

(II-2)
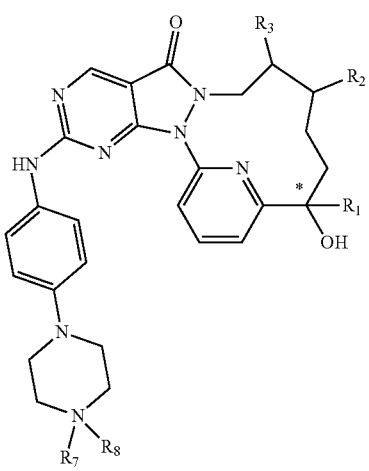
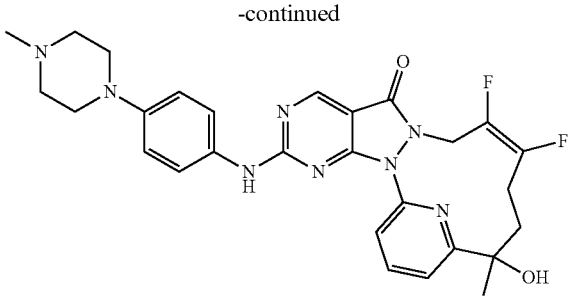
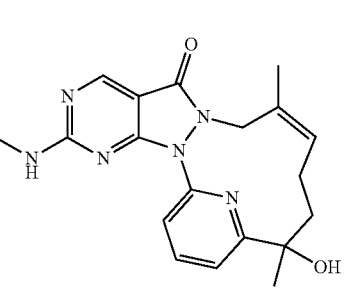
(III-A1)
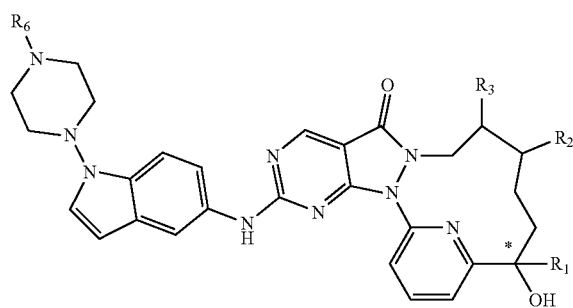
wherein, $R_1$, $R_2$, $R_3$, $R_6$, $R_7$ and $R_8$ are as defined herein;
the carbon atom with "*" is a chiral carbon atom, which is present in a form of a single enantiomer as (R) or (S) or in a form enriched with an enantiomer.
Provided is also a compound or an isomer or a pharmaceutically acceptable salt thereof, wherein the compound has the structure of
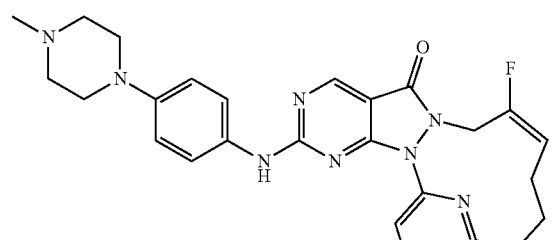
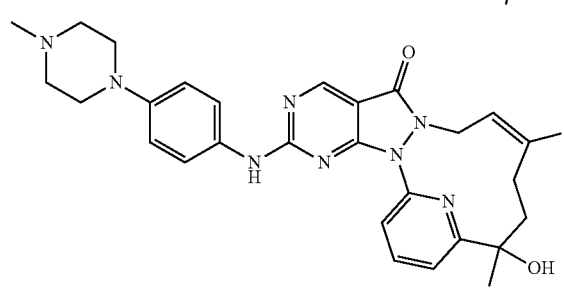
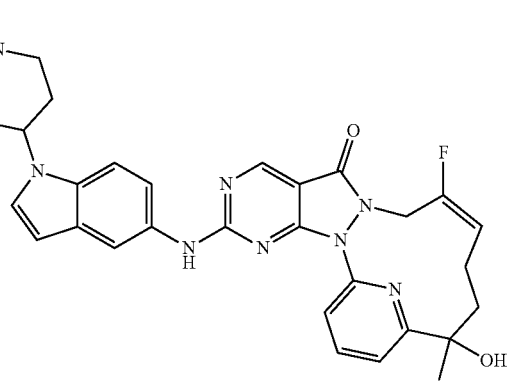

11
-continued
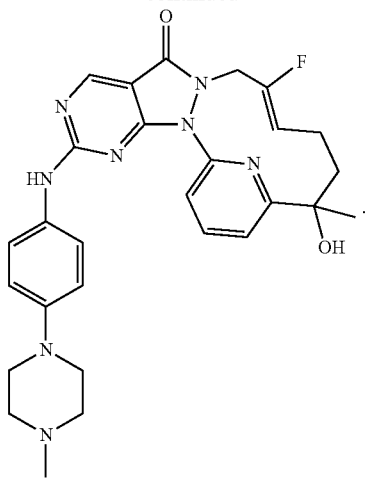
In some embodiments according to the present disclosure, provided is a compound or an isomer or a pharmaceutically acceptable salt thereof, wherein the compound has the structure of
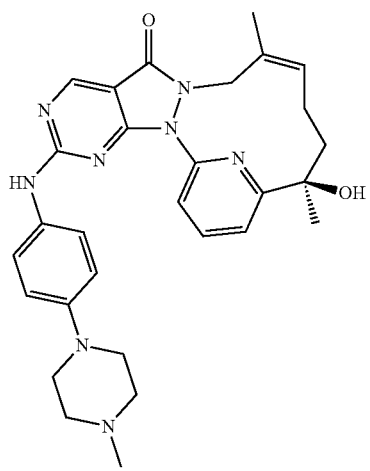
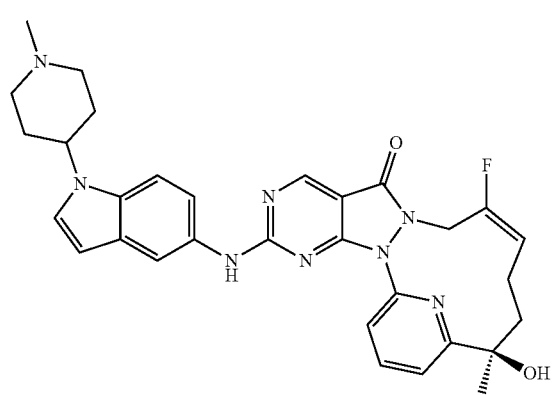
12
-continued
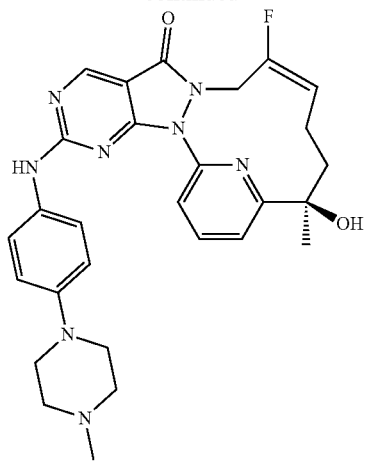
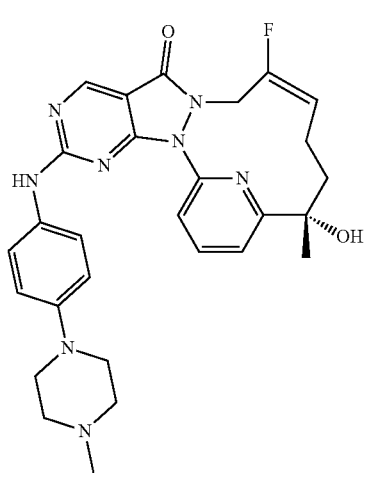
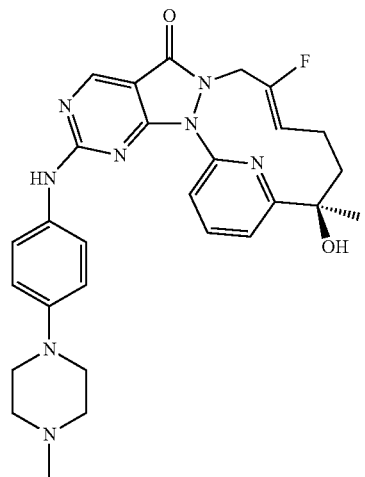

-continued

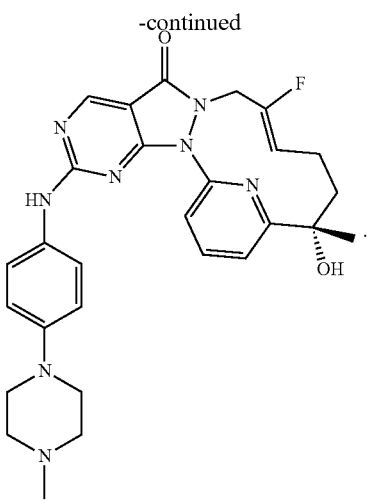

Provided is further use of the compound according to the present disclosure, or an isomer or a pharmaceutically acceptable salt thereof for the manufacture of a medicament for treating a Wee1 associated disease.

Technical Effect

As a new Wee1 inhibitor, the compounds of the present disclosure have good inhibitory effect on Wee1 kinase and good permeability. Regarding the pharmacokinetics, the compounds of the present disclosure have good indicator in many aspects, including significant advantages in in vivo clearance, half-life, in vivo concentration integral and the bioavailability.

DETAILED DESCRIPTION

General Definition

Unless stated otherwise, the following terms and phrases have the following definitions. A specific term or phrase should not be considered as indefinite or unclear without specific definition and should be understood according to the normal meanings. A tradename used herein shall refer to the corresponding article or the active ingredient.

The term "pharmaceutically acceptable" means that, for the compounds, materials, compositions and/or dosage form, with reliable medical judgement, they are suitable for use in contact with tissues of humans and animals without excessive toxicity, irritation, allergic reaction or other problems or complications and commensurate with a reasonable benefit/risk ratio.

The term "pharmaceutically acceptable salt" refers to a salt of the compound of the present disclosure, which is prepared using a compound found in the present disclosure which has a specific substituent with a relatively non-toxic acid or base. When the compound of the present disclosure contains a relatively acidic functional group, the base addition salt can be obtained by contacting the neutral form of such compound with a sufficient amount of base in a pure solution or a suitable inert solvent. Pharmaceutically acceptable base addition salts include sodium, potassium, calcium, ammonium, organic amine or magnesium salt or the like. When the compound of the present disclosure contains a relatively basic functional group, the acid addition salt can be obtained by contacting the neutral form of such compound with a sufficient amount of acid in a pure solution or a suitable inert solvent. Examples of pharmaceutically acceptable acid addition salts include inorganic acid salts including, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, etc.; and organic acid salts including, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid, etc.; and also includes salts of amino acids (such as arginine, etc.), and salts of organic acids such as glucuronic acid. Some specific compounds of the present disclosure contain basic and acidic functional groups, which can be converted to any base or acid addition salt.

The pharmaceutically acceptable salts of the present disclosure can be synthesized from the parent compound containing acid radicals or basic groups by conventional chemical processes. In general, the preparation process of such salts is: in water or an organic solvent or a mixture thereof, by reacting these compounds in free acid or base form with a stoichiometric amount of appropriate base or acid.

The compounds of the present disclosure may exist in specific geometric or stereoisomer forms. The present disclosure encompasses all such compounds, including cis and trans isomers, (−)- and (+)-enantiomers, (R)- and (S)-enantiomers, diastereomers, (D)-isomer, (L)-isomer, and their racemic mixtures and other mixtures, such as enantiomer or diastereomer-enriched mixtures. All of these mixtures are included within the scope of the present disclosure. There may be additional asymmetric carbon atoms in alkyl and other substituents. All these isomers and mixtures thereof are included in the scope of the present disclosure.

Unless stated otherwise, the term "enantiomer" or "optical isomer" refers to stereoisomers that are mirror images to each other.

Unless stated otherwise, the term "cis-trans isomer" or "geometric isomer" is caused by a double bond or a single bond of the ring-forming carbon atom which cannot rotate freely.

Unless stated otherwise, the term "diastereomer" refers to a stereoisomer in which the molecule has two or more chiral centers and there is a non-mirror relationship between the molecules.

Unless stated otherwise, "(+)" means right-handed, "(−)" means left-handed, and "(±)" means racemic.

Unless stated otherwise, the wedge-shaped solid line bond ( ◢ ) and the wedge-shaped dotted line bond ( ◌ ) indicate the absolute configuration of a stereocenter; the straight solid line bond ( ◢ ) and the straight dotted line bond ( ◌ ) indicate the relative configuration of a stereocenter; and the wavy line ( ∿ ) indicates a wedge-shaped solid line bond ( ◢ ) or a wedge-shaped dotted line bond ( ◌ ), or a wavy line ( ∿ ) indicates a straight solid line bond ( ◢ ) and a straight dotted line bond ( ◌ ).

Unless stated otherwise, when there is a double bond(s) in a compound, such as carbon-carbon double bond, carbon-nitrogen double bond and nitrogen-nitrogen double bond, and each of the atoms on the double bond is connected to two different substituents (in a double bond containing nitrogen atom, the lone-pair electrons on the nitrogen atom is considered as a substituent to which is connected), if the atom on the double bond is connected to its substituent via a wavy line ( ∿ ), it refers to (Z) isomer, (E) isomer or a mixture thereof. For example, the following formula (A) means the compound exists as a single isomer of formula (A-1) or formula (A-2) or as a mixture of two isomers of formula (A-1) and formula (A-2); the following formula (B) means the compound exists as a single isomer of formula (B-1) or formula (B-2) or as a mixture of two isomers of formula (B-1) and formula (B-2); and the following formula (C) means the compound exists as a single isomer of formula (C-1) or formula (C-2) or as a mixture of two isomers of formula (C-1) and formula (C-2).

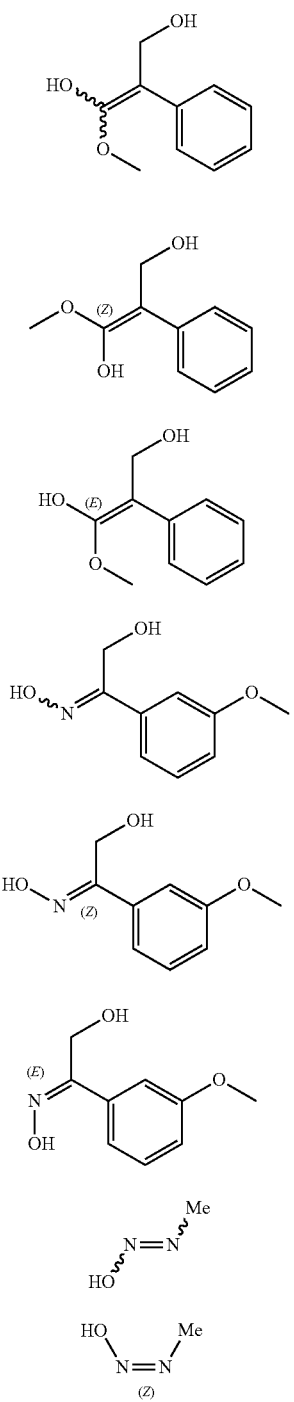

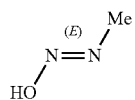

The present compounds may be present in particular tautomeric forms. Unless stated otherwise, the term "tautomer" or "tautomeric form" means that at room temperature, different functional groups of an isomer are in dynamic equilibrium and can be transformed to each other quickly. If a tautomer is possible (e.g., in solution), the chemical equilibrium of tautomers can be achieved. For example, proton tautomer (also known as prototropic tautomer) includes interconversion through protolysis, such as ketone-enol isomerization and imine-enamine isomerization. The valence tautomer includes some recombination of bonding electrons for interconversion. A specific example of keto-enol tautomerization is the interconversion between two tautomers pentane-2,4-dione and 4-hydroxypent-3-en-2-one.

Unless stated otherwise, the term "enriched with an isomer", "isomer enriched", "enriched with an enantiomer" or "enantiomerically enriched" means that the content of an isomer or enantiomer is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless stated otherwise, the term "isomer excess" or "enantiomeric excess" refers to the difference between the relative percentages of two isomers or two enantiomers. For example, if the content of one isomer or enantiomer is 90% and the content of the other isomer or enantiomer is 10%, the excess of isomer or enantiomer (ee value) is 80%.

The optically active (R)- and (S)-isomers and D and L isomers can be prepared by chiral synthesis or chiral reagents or other conventional techniques. If an enantiomer of a compound of the present disclosure is desired, it can be prepared by asymmetric synthesis or derivatization with a chiral auxiliary, wherein the resulting mixture of diastereomers is separated and the auxiliary group is cleaved to provide pure and required enantiomer. Alternatively, when the molecule contains a basic functional group (such as amino) or an acidic functional group (such as, carboxyl group), a diastereomer salt is formed with an appropriate optically active acid or base, and the diastereomer resolution is performed by conventional processes known in the art, and then the pure enantiomer is recovered. In addition, the separation of enantiomers and diastereomers is usually accomplished by using chromatography, which employs a chiral stationary phase optionally with chemical derivatization processes (e.g., carbamate formation from amine). The present compounds may contain unnatural proportions of atomic isotopes at one or more of the atoms constituting the compound. For example, compounds can be labeled with radioactive isotopes, such as tritium ($^3$H), iodine-125 ($^{125}$I) or C-14 ($^{14}$C). As another example, hydrogen can be replaced by heavy hydrogen to form a deuterated drug. The bond formed by deuterium and carbon is stronger than that formed by ordinary hydrogen and carbon. Compared with non-deuterated drugs, the deuterated drugs have advantages such as less side effects, increased stability, improved efficacy, prolonged biological half-life and the like. Alternation of all the radioisotopes of the compound, either radioactive or not, is encompassed within the scope of the invention.

"Optional" or "optionally" means that the subsequently described event or condition may but does not necessarily occur, and the description includes the situation in which the event or condition occurs and the situation in which the event or condition does not occur.

The term "substituted" means any one or more hydrogen atoms on a specific atom are replaced by a substituent, which may include heavy hydrogen and hydrogen variants, provided that the valence state of the specific atom is normal and the compound after substitution is stable. A substituent as oxygen (i.e. =O) means two hydrogen atoms are substituted. Oxygen substitution will not occur on an aromatic group. The term "optional substitution" or "optionally substituted" encompasses the cases that being unsubstituted or substituted. Unless stated otherwise, the type and number of substituents may be arbitrary given that they can be achieved chemically.

When any variable (e.g., R) appears more than once in the composition or structure of a compound, it is defined independently in each case. Thus, for example, if a group is substituted with 0-2 R, the group can be optionally substituted with at most two R, and R in each case has independent options. In addition, combinations of substituents and/or their variants are allowed provided that such combinations will produce stable compounds.

When the number of a linking group is 0, —(CRR)$_0$—, it means that the linking group is a single bond.

When one of the variables is selected from the group consists of single bonds, it means that the two groups connected thereby are directly connected. For example, when L represents a single bond in A-L-Z, the actual structure is A-Z. When a substituent is absent, it means that the substituent does not exist. For example, when X is absent in A-X, it means that the actual structure is A.

Unless stated otherwise, the number of atoms in the ring is usually defined as the member number of the ring. For example, "5-7 membered ring" refers to 5-7 atoms which are arranged around.

Unless stated otherwise, a "4-10 membered ring" refers to cycloalkyl, heterocycloalkyl, cycloalkenyl, heterocycloalkenyl, cycloalkynyl, heterocycloalkynyl, aryl or heteroaryl, which is composed of 4-10 ring atoms. The ring includes single ring, and also includes bicyclic or polycyclic ring systems, such as spiro ring, fused ring, bridge ring or the like. Unless stated otherwise, the ring optionally contains 1, 2 or 3 heteroatoms independently selected from the group consisting of O, S and N. The 4-10 membered ring comprises 4-9 membered, 4-8 membered, 4-7 membered, 4-6 membered ring, 4-10 membered, 4-9 membered, 4-8 membered and 4-7 membered ring or the like. The "4-7 membered ring" comprises e.g. phenyl, pyridyl, piperidinyl or the like. On the other hand, the term "4-7 membered heterocycloalkyl" comprises piperidinyl or the like but does not comprises phenyl. The term "ring" also includes a ring system containing at least one ring, wherein each "ring" independently complies with the above definition.

Unless stated otherwise, a "5-12 membered ring" refers to cycloalkyl, heterocycloalkyl, cycloalkenyl, heterocycloalkenyl, cycloalkynyl, heterocycloalkynyl, aryl or heteroaryl, which is composed of 5-12 ring atoms. The ring includes single ring, and also includes bicyclic or polycyclic ring systems, such as spiro ring, fused ring, bridge ring or the like. Unless stated otherwise, the ring optionally contains 1, 2 or 3 heteroatoms independently selected from the group consisting of O, S and N. The 5-12 membered ring comprises 5-10 membered, 5-9 membered, 5-8 membered, 5-7 membered, 5-6 membered, 6-10 membered, 6-9 membered, 6-8 membered, 6-7 membered ring or the like. The "5-7 membered ring" comprises e.g. phenyl, pyridyl, piperidinyl or the like. On the other hand, the term "5-7 membered heterocycloalkyl" comprises piperidinyl or the like but does not comprise phenyl. The term "ring" also includes a ring system containing at least one ring, wherein each "ring" independently complies with the above definition.

Unless stated otherwise, a "6-12 membered ring" refers to cycloalkyl, heterocycloalkyl, cycloalkenyl, heterocycloalkenyl, cycloalkynyl, heterocycloalkynyl, aryl or heteroaryl, which is composed of 6-12 ring atoms. The ring includes single ring, and also includes bicyclic or polycyclic ring systems, such as spiro ring, fused ring, bridge ring or the like. Unless stated otherwise, the ring optionally contains 1, 2 or 3 heteroatoms independently selected from the group consisting of O, S and N. The 6-12 membered ring comprises 6-10 membered, 6-9 membered, 6-8 membered, 6-7 membered ring or the like. The "5-7 membered ring" comprises e.g. phenyl, pyridyl, piperidinyl or the like. On the other hand, the "5-7 membered heterocycloalkyl" comprises piperidinyl or the like but does not comprise phenyl. The term "ring" also includes a ring system containing at least one ring, wherein each "ring" independently complies with the above definition.

Unless stated otherwise, a "5-10 membered ring" refers to cycloalkyl, heterocycloalkyl, cycloalkenyl, heterocycloalkenyl, cycloalkynyl, heterocycloalkynyl, aryl or heteroaryl, which is composed of 5-10 ring atoms. The ring includes single ring, and also includes bicyclic or polycyclic ring systems, such as spiro ring, fused ring, bridge ring or the like. Unless stated otherwise, the ring optionally contains 1, 2 or 3 heteroatoms independently selected from the group consisting of O, S and N. The 5-10 membered ring comprises 5-9 membered, 5-8 membered, 5-7 membered, 5-6 membered ring, 6-10 membered, 6-9 membered, 6-8 membered, 6-7 membered ring or the like. The "5-7 membered ring" comprises, e.g. phenyl, pyridyl, piperidinyl or the like. On the other hand, the "5-7 membered heterocycloalkyl" comprises piperidinyl or the like but does not comprise phenyl. The term "ring" also includes a ring system containing at least one ring, wherein each "ring" independently complies with the above definition.

Unless stated otherwise, "5-8 membered ring" refers to cycloalkyl, heterocycloalkyl, cycloalkenyl, heterocycloalkenyl, cycloalkynyl, heterocycloalkynyl, aryl, or heteroaryl, which is composed of 5-8 ring atoms. The ring includes single ring, and also includes bicyclic ring systems, such as spiro ring, fused ring, bridge ring or the like. Unless stated otherwise, the ring optionally contains 1, 2 or 3 heteroatoms independently selected from the group consisting of O, S and N. The 5-8 membered ring comprises 5-7 membered, 6-8 membered, 6-7 membered or the like. The "5-7 membered ring" comprises e.g. phenyl, pyridyl, piperidinyl or the like. On the other hand, the term "5-7 membered heterocycloalkyl" comprises piperidinyl or the like but does not comprise phenyl. The term "ring" also includes a ring system containing at least one ring, wherein each "ring" independently complies with the above definition.

Unless stated otherwise, "5-6 membered ring" refers to cycloalkyl, heterocycloalkyl, cycloalkenyl, heterocycloalkenyl, cycloalkynyl, heterocycloalkynyl, aryl or heteroaryl, which is composed of 5-6 ring atoms. The ring includes single ring, and also includes bicyclic ring systems, such as spiro ring, fused ring, bridge ring or the like. Unless stated otherwise, the ring optionally contains 1, 2 or 3 heteroatoms independently selected from the group consisting of O, S and N. The 5-6 membered ring comprises 5 membered, 6 membered ring or the like. The "5-6 membered ring" comprises e.g. phenyl, pyridyl, piperidinyl or the like. On the other hand, the term "5-6 membered heterocycloalkyl" comprises piperidinyl or the like but does not comprise phenyl. The term "ring" also includes a ring system containing at least one ring, wherein each "ring" independently complies with the above definition.

Unless stated otherwise, the term "$C_{1-3}$ alkyl" refers to a linear or branched saturated hydrocarbon group composed of 1-3 carbon atoms. The $C_{1-3}$ alkyl comprises $C_{1-2}$, $C_{2-3}$ alkyl or the like; which may be monovalent (e.g. methyl), divalent (e.g. methylene) or polyvalent (e.g. methyne). Examples of $C_{1-3}$ alkyl comprise but not limited to methyl (Me), ethyl (Et), propyl (including n-propyl and isopropyl) or the like.

Unless stated otherwise, the term "$C_{1-3}$ alkoxy" refers to an alkyl group containing 1-3 carbon atoms connected to the rest of the molecule via an oxygen atom. The $C_{1-3}$ alkoxy comprises $C_{1-2}$, $C_{2-3}$, $C_3$ and $C_2$ alkoxy or the like. Examples of $C_{1-3}$ alkoxy include but are not limited to methoxyl, ethoxy, propoxy (including n-propoxy and isopropoxy), or the like.

Unless stated otherwise, the term "$C_{1-3}$ alkylamino" refers to an alkyl group containing 1-3 carbon atoms connected to the rest of the molecule via an amino group. The $C_{1-3}$ alkylamino comprises $C_{1-2}$, $C_3$, $C_2$ alkylamino or the like. Examples of $C_{1-3}$ alkylamino comprise but not limited to —NHCH$_3$, —N(CH$_3$)$_2$, —NHCH$_2$CH$_3$, —N(CH$_3$)CH$_2$CH$_3$, —NHCH$_2$CH$_2$CH$_3$, —NHCH$_2$(CH$_3$)$_2$ or the like.

Unless stated otherwise, "$C_{3-8}$ cycloalkyl" refers to a saturated cyclic hydrocarbon group composed of 3-8 carbon atoms, including single ring and bicyclic system, wherein the bicyclic system comprises spiro ring, fused ring and bridge ring. The $C_{3-8}$ cycloalkyl comprises $C_{3-6}$, $C_{3-5}$, $C_{4-8}$, $C_{4-6}$, $C_{4-5}$, $C_{5-8}$, $C_{5-6}$ cycloalkyl or the like. The cycloalkyl may be monovalent, divalent or polyvalent. Examples of $C_{3-8}$ cycloalkyl include but are not limited to cyclopropyl, cyclobutyl, cyclopentyl, cyclohexyl, cycloheptyl, norbornyl alkyl, [2.2.2]bicyclooctane or the like.

Unless stated otherwise, the term "4-10 membered heterocycloalkyl" alone or in combination with another term, refers to a saturated cyclic group composed of 4-10 ring atoms, wherein 1, 2, 3 or 4 ring atoms are heteroatoms independently selected from the group consisting of O, S and N, and the rest are carbon atoms, wherein the nitrogen atom is optionally quaternarized, and wherein the nitrogen and sulfur heteroatoms are optionally oxidized (i.e. NO and S(O)$_p$, p is 1 or 2). The "4-10 membered heterocycloalkyl" comprises single ring, bicyclic and tricyclic ring system, wherein the bicyclic and tricyclic ring system comprises spiro ring, fused ring and bridge ring. In addition, with respect to the "4-10 membered heterocycloalkyl", the heteroatom may be at the position where the heterocycloalkyl is contented to rest of the molecule. The 4-10 membered heterocycloalkyl comprise 4-8 membered, 4-6 membered, 4-5 membered, 5-6 membered, 4 membered, 5 membered, 6 membered heterocycloalkyl or the like. Examples of 4-10 membered heterocycloalkyl comprise but not limited to azetidinyl, oxetanyl, thietanyl, pyrrolidinyl, pyrazolidinyl, imidazolidinyl, tetrahydrothienyl (including tetrahydrothien-2-yl and tetrahydrothien-3-yl or the like), tetrahydrofuranyl (including tetrahydrofuran-2-yl or the like), tetrahydropyranyl, piperidinyl (including 1-piperidinyl, 2-piperidinyl and 3-piperidinyl or the like), piperazinyl (including 1-piperazinyl and 2-piperazinyl or the like), morpholinyl (including 3-morpholinyl and 4-morpholinyl or the like), dioxanyl, dithianyl, isoxazolealkyl, isothiazolidinyl, 1,2-oxazinyl, 1,2-thiazinyl, hexahydropyridazinyl, homopiperazinyl, homopiperidinyl or dioxepanyl and the like.

Unless stated otherwise, the terms "5-12 membered heteroaromatic ring" and "5-12 membered heteroaryl" can be used interchangeably herein. The term "5-12 membered heteroaryl" refers to a cyclic group with conjugated π electron system composed of 5-12 ring atoms, wherein 1, 2, 3 or 4 ring atoms are heteroatoms independently selected from the group consisting of O, S and N, and the rest are carbon atoms. The "5-12 membered heteroaryl" can be a single ring, a fused bicyclic or a fused tricyclic ring system, wherein each of the ring is aromatic and wherein the nitrogen atom is optionally quaternarized, and wherein the nitrogen and sulfur heteroatoms are optionally oxidized (i.e. NO and S(O)$_p$, p is 1 or 2). The 5-12 membered heteroaryl can be connected to the rest of the molecule via the heteroatom or carbon atom. The 5-12 membered heteroaryl comprises 5-10 membered, 5-8 membered, 5-7 membered, 5-6 membered, 5 membered, 6 membered heteroaryl or the like. Examples of the 5-12 membered heteroaryl comprise but not limited to pyrrolyl (including N-pyrrolyl, 2-pyrrolyl and 3-pyrrolyl or the like), pyrazolyl (including 2-pyrazolyl and 3-pyrazolyl or the like), imidazolyl (including N-imidazolyl, 2-imidazolyl, 4-imidazolyl and 5-imidazolyl or the like), oxazolyl (including 2-oxazolyl, 4-oxazolyl and 5-oxazolyl or the like), triazolyl (1H-1,2,3-triazolyl, 2H-1,2,3-triazolyl, 1H-1,2,4-triazolyl and 4H-1,2,4-triazolyl or the like), tetrazolyl, isoxazolyl (3-isoxazolyl, 4-isoxazolyl and 5-isoxazolyl or the like), thiazolyl (including 2-thiazolyl, 4-thiazolyl and 5-thiazolyl or the like), furyl (including 2-furyl and 3-furyl or the like), thienyl (including 2-thienyl and 3-thienyl or the like), pyridyl (including 2-pyridyl, 3-pyridyl and 4-pyridyl or the like), pyrazinyl, pyrimidinyl (including 2-pyrimidinyl and 4-pyrimidinyl or the like), benzothiazolyl (including 5-benzothiazolyl or the like), purinyl, benzimidazolyl (including 2-benzimidazolyl or the like), benzoxazolyl, indolyl (including 5-indolyl or the like), isoquinolinyl (including 1-isoquinolinyl and 5-isoquinolinyl or the like), quinoxalinyl (including 2-quinoxalinyl and 5-quinoxalinyl or the like) or quinolinyl (including 3-quinolinyl and 6-quinolinyl or the like).

Unless stated otherwise, the terms "$C_{6-10}$ aromatic ring" and "$C_{6-10}$ aryl" can be used interchangeably herein. The term "$C_{6-10}$ aromatic ring" or "$C_{6-10}$ aryl" refers to a cyclic hydrocarbon group with conjugated π electron system composed of 6-10 carbon atoms. The "$C_{6-10}$ aromatic ring" or "$C_{6-10}$ aryl" can be a single ring, a fused bicyclic or a fused tricyclic ring system, wherein each of the ring is aromatic, and can be monovalent, divalent or polyvalent. The $C_{6-10}$ aryl comprises $C_{6-9}$, $C_9$, $C_{10}$, $C_6$ aryl or the like. Examples of $C_{6-10}$ aryl comprise but not limited to phenyl, naphthyl (including 1-naphthyl, 2-naphthyl or the like).

Unless stated otherwise, the term "$C_{6-8}$ aromatic ring" and "$C_{6-8}$ aryl" can be used interchangeably herein, The term "$C_{6-8}$ aromatic ring" or "$C_{6-8}$ aryl" refers to a cyclic hydrocarbon group with conjugated π electron system composed of 6-8 carbon atoms. The "$C_{6-8}$ aromatic ring" or "$C_{6-8}$ aryl" can be a single ring, a fused bicyclic or a fused tricyclic ring system, wherein each of the ring is aromatic and can be monovalent, divalent or polyvalent. $C_{6-8}$ aryl comprises $C_6$ aryl or the like. Examples of $C_{6-8}$ aryl comprise but not limited to phenyl.

Unless stated otherwise, $C_{n-n+m}$ or $C_n$-$C_{n+m}$ includes any specific case of n to n+m carbon. For example, $C_{1-12}$ comprises $C_1$, $C_2$, $C_3$, $C_4$, $C_5$, $C_6$, $C_7$, $C_8$, $C_9$, $C_{10}$, $C_{11}$, and $C_{12}$ and also comprises any range within n to n+m, for example, $C_{1-12}$ comprises $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$ or the like. Likewise, n membered to n+m membered means that the atom number in the ring is n to n+m, for example, 3-12 membered ring comprises 3 membered ring, 4 membered ring, 5 membered ring, 6 membered ring, 7 membered ring, 8 membered ring, 9 membered ring, 10 membered ring, 11 membered ring, and 12 membered ring, and also comprises any range within n to n+m, for example, 3-12 membered ring comprises 3-6 membered ring, 3-9 membered ring, 5-6 membered ring, 5-7 membered ring, 6-7 membered ring, 6-8 membered ring, and 6-10 membered ring or the like.

The term "leaving group" refers to a functional group or atom which can be replaced by another functional group or atom through substitution reaction (e.g., affinity substitution reaction). For example, representative leaving groups include triflate; Cl, Br, I; sulfonate, such as mesylate, tosylate, p-bromobesylate, p-toluenesulfonate or the like; acyloxy, such as acetoxy, trifluoroacetoxy, or the like.

The term "protecting group" includes but are not limited to "amino protecting group", "hydroxyl protecting group" or "mercapto protecting group". The term "amino protecting group" refers to a protecting group suitable for preventing side reactions on the nitrogen position of an amino group. Representative amino protecting groups include but are not limited to formyl; acyl, such as alkanoyl (such as acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorene methoxycarbonyl (Fmoc); arylmethyl, such as benzyl (Bn), triphenylmethyl (Tr), 1,1-bis-(4'-methoxylphenyl)methyl; silyl, such as trimethylsilyl (TMS) and tert-butyldimethylsilyl (TBS), or the like. The term "hydroxyl protecting group" refers to a protecting group suitable for preventing hydroxyl side reactions. Representative hydroxyl protecting groups include but are not limited to alkyl, such as methyl, ethyl and tert-butyl; acyl, such as alkanoyl (such as acetyl); arylmethyl, such as benzyl (Bn), p-methoxylbenzyl (PMB), 9-fluorenylmethyl (Fm) and diphenylmethyl (benzhydryl, DPM); methylsilyl, such as trimethylsilyl (TMS) and tert-butyldimethylsilyl (TBS), or the like.

The present compound can be confirmed with the structure by conventional methods well known to a person skilled in the art. If the present compound relates to an absolute configuration, it can be confirmed by conventional technical means in the art. For example, the single crystal X-ray diffraction method (SXRD) can be used, where the Bruker D8 venture diffractometer is used to collect the diffraction intensity data of the cultivated single crystal, the light source is CuKα radiation, the scanning method is φ/ω scanning. After the relevant data is collected, the direct method is further used (Shelxs97) to analyze the crystal structure, and the absolute configuration can be confirmed.

The present compounds can be prepared by various synthetic processes well-known to a person skilled in the art, including the specific embodiments listed below. The embodiments formed by the combination with other chemical synthesis processes and equivalence well-known to a person skilled in the art and preferable embodiments include but are not limited to Example herein.

The present compounds may have multiple applications or indications, including but not limited to those specifically listed herein.

The solvents used herein are commercially available. The following abbreviations are used herein: aq: water; ACN: acetonitrile; Tris-HCl: Tris (hydroxymethyl) aminomethane hydrochloride salt; EDTA: ethylenediaminetetraacetic acid; m-CPBA: meta-chloroperbenzoic acid; $NH_3H_2O$: ammonia; DEA: diethanolamine; IPA: isopropanol.

EXAMPLES

The present disclosure will be described in detail by the following Examples, which do not mean any limitation thereto. The present disclosure has been described in detail herein, which also discloses its specific embodiments. It will be apparent for a person skilled in the art that various changes and modifications can be made to specific embodiments of the present disclosure without departing from its spirit and scope.

Intermediate 1

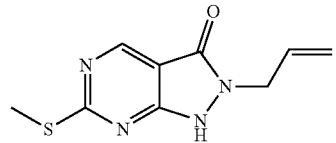

1-N was prepared by referring to the synthesis process of WO2007126122.

Example 1: Compound 1

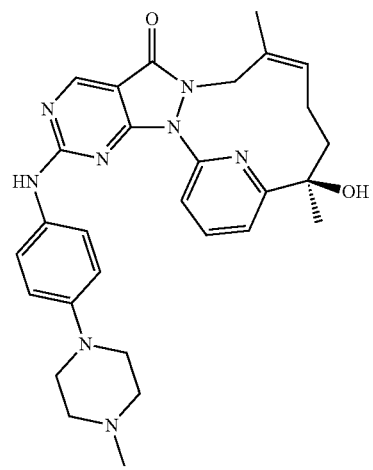

Synthesis Scheme:

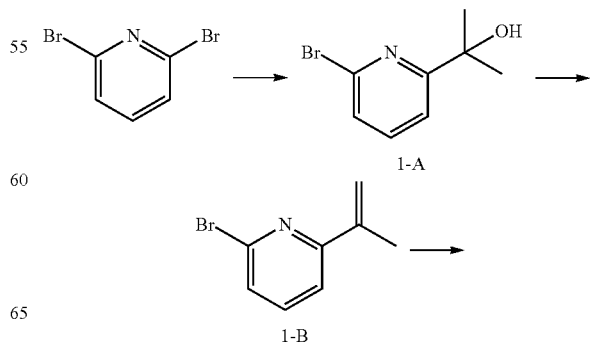

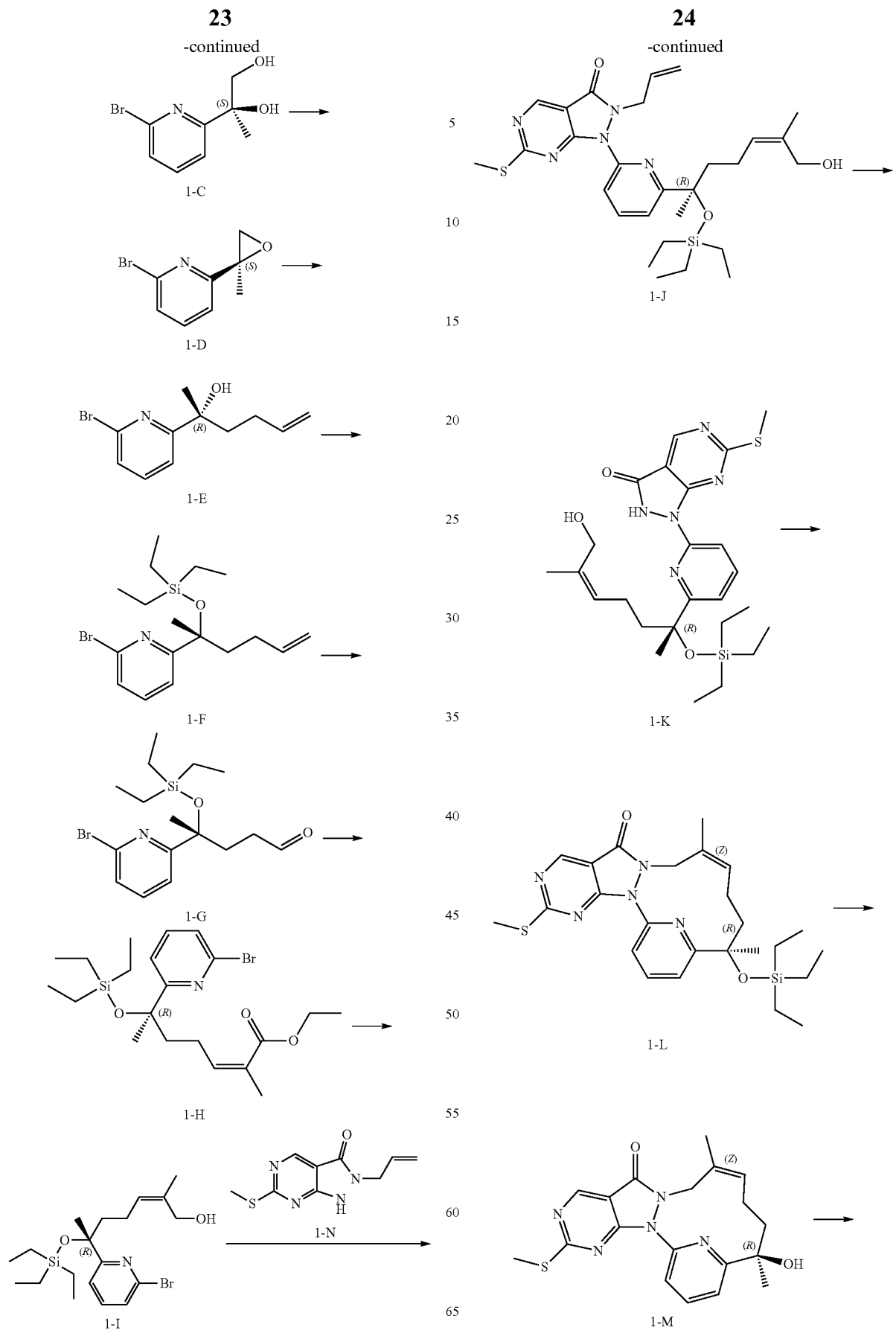

-continued

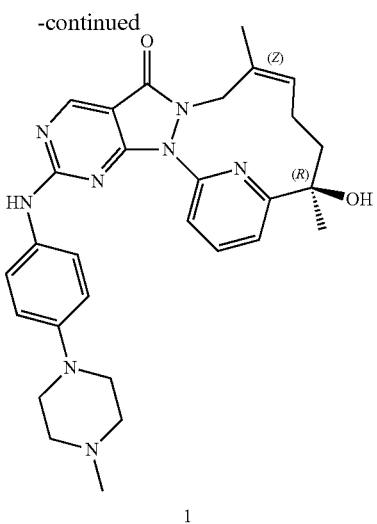

1

Step 1: Synthesis of Compound 1-A

At 20-30° C., to a 5 L 4-necked flask was added 2.5 L of dichloromethane, to which was then added 2,6-dibromopyridine (500 g, 2.11 mol). The reaction mixture was purged with nitrogen three times and cooled to −60 to −70° C. with dry ice ethanol. The temperature was controlled as −60 to −70° C. and 886.5 mL of n-butyllithium (2 M) was added dropwise. After addition, the reaction was performed at −60 to −70° C. for 1 h. Acetone (233 mL, 3.17 mol) was added and after addition, the reaction was performed under controlled temperature for 20-30 min. High-performance Liquid Chromatographer was used to monitor the reaction till completion. To the system was added 250 mL saturated ammonium chloride solution to quench the reaction and the system was warmed to room temperature, to which was added 1.6 L of water with stirring for 10 min. The reaction system was allowed to stand for liquid separation. The organic phase was washed with 1.6 L of water and concentrated with drying to give 1-A as black liquid which was directly used for the next step.

Step 2: Synthesis of Compound 1-B

At 20-30° C., to a 5 L three-necked bottle was added 1.75 L of concentrated sulfuric acid, to which was added dropwise 1-A (1.75 kg, 8.10 mol) with the temperature maintained ≤60° C. After addition, the system was maintained at 50-60° C. and reacted for 12 h. High-performance Liquid Chromatographer was used to monitor the reaction till completion. The reaction liquid was cooled to room temperature and was poured into 6 Kg ice water. 6 N sodium hydroxide solution was used to adjust pH to 9-10. The reaction system was extracted with 10 L n-heptane for liquid separation. The organic phase was concentrated under reduced pressure to give the crude product, which was subjected to flash silica pad (n-heptane rinsing) to give 1-B as yellow liquid.

Step 3: Synthesis of Compound 1-C

At 20-30° C., to a 50 L spherical kettle was added 10 L of tert-butyl alcohol and 10 L of water. Under stirring, anhydrous potassium carbonate (1.74 kg, 12.59 mol), red potassium (4.16 kg, 12.59 mol), potassium osmate dihydrate (3.72 g, 0.01 mol) and hydroquinidine 1,4-phthalazinediyl ether (19.67 g, 0.025 mol) were added. After addition, the reaction system was stirred at 20-30° C. for 10-20 min and then cooled to 0-15° C. with a ice water bath, to which was added compound 1-B (1 kg, 5.04 mol) and the reaction was performed under controlled temperature for 15-20 h. High-performance Liquid Chromatographer was used to monitor the reaction till completion. 10 L of saturated sodium sulfite solution was used to quench the reaction. 15 L of ethyl acetate was added, and the reaction was extracted for liquid separation. The organic phase was then washed with 15 L of saturated brine and concentrated under reduce pressure to give thick liquid. To the crude product was added 4 L of n-heptane, which was stirred at 0° C. for 1 h, filtered and the filter cake was dried to give compound 1-C.

Step 4: Synthesis of Compound 1-D

At 15-30° C., to a 50 L jacketed kettle was added 21 L of toluene, and 1,8-diazabicyclo[5.4.0]undec-7-ene (4.13 kg, 27.13 mol) and compound 1-C (2.1 kg, 9.04 mol) with stirring. The reaction system was cooled to 0-5° C., to which was added dropwise perfluoro-1-butanesulfonyl fluoride (4.24 kg, 14.01 mol). After addition, the reaction was maintained at 0-5° C. for 15-20 h. High-performance Liquid Chromatographer was used to monitor the reaction till completion. The reaction system was poured into 17.5 L of water to quench the reaction and allowed to stand for liquid separation. The aqueous phase was extracted with 8.8 L of toluene again for liquid separation. The organic phases were combined, washed with water (15.8 L*2), concentrated under reduced pressure till no fraction to give 1-D as black liquid.

Step 5: Synthesis of Compound 1-E

At 20-30° C., a 5 L dry and clean three-necked bottle was purged with nitrogen three times, to which was added allylmagnesium bromide (1 M ethyl ether solution, 1.64 L, 1.92 mol), and cooled with dry ice ethanol to <−60° C. A solution of compound 1-D (293 g, 1.37 mol) in 1 L dichloromethane was added dropwise with the temperature maintained <−50° C. throughout the procedure. After addition, the reaction was maintained as <−50° C. for 0.5-1 h. High-performance Liquid Chromatographer was used to monitor the reaction till completion. The reaction system was poured into 2.5 L of saturated ammonium chloride solution to quench the reaction and then 25-30% ammonia to adjust the pH to ≥10. 3.5 L of ethyl acetate was added with stirring and the reaction was allowed to stand for liquid separation. The organic phase was washed with 1 L of saturated brine, dried over anhydrous sodium sulfate, filtered, and rotated to dryness to give the crude product. The crude produce was subjected to flash silica pad (ethyl acetate: n-heptane=1:10) to give 1-E as brown liquid.

$^1$H NMR (DMSO-d$_6$): 7.71 (t, J=7.6 Hz, 1H), 7.64 (d, J=7.2 Hz, 1H), 7.44 (d, J=6.8 Hz, 1H), 5.69-5.78 (m, 1H), 5.25 (s, 1H), 4.84-4.93 (m, 2H), 1.67-2.04 (m, 4H), 1.42 (s, 3H).

Step 6: Synthesis of Compound 1-F

Compound 1-E (50.00 g, 164.58 mmol) and 2,6-dimethylpyridine (21.16 g, 197.50 mmol, 23.00 mL) were added into dichloromethane (500 mL), which was cooled to −10° C. to 0° C. with dry ice. To the reaction system was then added slowly triethylsilyl trifluoromethanesulfonate (56.56 g, 213.95 mmol, 48.34 mL), which was stirred at −10° C. to 0° C. for 2.5 h. The reaction liquid was extracted with saturated citric acid solution (500 mL*2). The organic phase was washed with water (500 mL*1) and the lower layer of organic phase (500 mL) was obtained as a solution of compound 1-F in dichloromethane which was used directly for the next step.

Step 7: Synthesis of Compound 1-G

A solution of raw material compound 1-F in dichloromethane (500 mL) (60.96 g, 164.58 mmol) was cooled to −40° C. with dry ice ethanol bath, ozone was introduced under open state and reaction was performed for 2.5 h. After the reaction was completed, oxygen was introduced under open state for 40 min and then nitrogen was introduced under open state for 20 min. At −40° C., to the reaction system was slowly added triphenylphosphine (47.48 g, 181.04 mmol). After addition, the reaction system returned slowly to 20° C. and reaction was performed for 12 h. After the reaction was completed, the reaction liquid was concentrated under reduced pressure and rotated to dryness to give the crude product. The crude product was added into ethyl acetate (80 mL), to which was added slowly petroleum ether (300 mL) with stirring (with thick substance precipitated). The reaction mixture was filtered and the filtrate was concentrated under reduced pressure and rotated till no fraction, with solid precipitated. To the crude product after rotation was added again petroleum ether (300 mL) with stirring for 10 min, which was filtered. The filtrate was concentrated under reduced pressure and rotated till no fraction to give the crude product. The crude product was subjected to flash column chromatography for separation (silica gel mesh: 100-200, dichloromethane:petroleum ether=3:1) to give the target compound 1-G.

$^1$H NMR (400 MHz, CHCl$_3$-d) δ ppm 9.65 (s, 1H) 7.44-7.60 (m, 2H) 7.31 (d, J=7.58 Hz, 1H) 2.29-2.41 (m, 2H) 2.02-2.14 (m, 2H) 1.68 (s, 3H) 0.92-1.02 (m, 9H) 0.66 (q, J=7.91 Hz, 6H). MS-ESI m/z: 372.0[M+H]$^+$, MS-ESI m/z: 374.0[M+H]$^+$.

Step 8: Synthesis of Compound 1-H

The compound triethyl 2-phosphonopropionate (7.68 g, 32.23 mmol, 7.04 mL) was dissolved in tetrahydrofuran (100 mL), which was purged with nitrogen three times. The temperature was lowered to −70° C. with dry ice acetone and n-butyllithium (2.5 M, 12.89 mL, 1.2 eq) was added dropwise slowly to the reaction system with the temperature maintained no higher than −70° C. After addition, the reaction was performed under controlled temperature for 1 h. After the reaction was completed, to the reaction liquid was slowly added saturated ammonium chloride solution (100 mL), which was allowed to stand for liquid separation. The aqueous phase was again extracted with ethyl acetate (100 mL*1). The organic phases were combined, washed with water (100 mL*1) and then washed with saturated brine (120 mL*1). The organic phases were added with anhydrous sodium sulfate for drying and filtered. The filtrate was concentrated under reduced pressure and rotated till no fraction to give the crude product. The crude product was subjected to flash column chromatography for separation (silica gel mesh: 200-300, petroleum ether:ethyl acetate=70:1) to give the target compound 1-H.

$^1$H NMR (400 MHz, CHCl$_3$-d) δ ppm 7.72 (d, J=7.72 Hz, 1H) 7.58-7.64 (m, 1H) 7.41 (d, J=7.72 Hz, 1H) 5.83-5.90 (m, 1H) 4.20-4.31 (m, 2H) 2.48-2.61 (m, 1H) 2.17-2.35 (m, 2H) 1.93 (s, 3H) 1.84-1.91 (m, 1H) 1.77 (s, 3H) 1.34 (t, J=7.06 Hz, 3H) 1.08-1.14 (m, 9H) 0.79 (q, J=8.09 Hz, 6H). MS-ESI m/z: 457.9[M+H]$^+$.

Step 9: Synthesis of Compound 1-I

Compound 1-H (3.17 g, 6.94 mmol) was added into dichloromethane (30 mL), which was purged with nitrogen three times and cooled to 0° C. with ice-salt bath. To the reaction system was added dropwise slowly diisobutylaluminium hydride (1 M, 17.36 mL) with the temperature maintained as −5° C. to 0° C. After addition, the reaction system was warmed to room temperature of 19° C. and maintained for 12 h. After the reaction was completed, saturated potassium sodium tartrate solution (50 mL) was added dropwise slowly to the reaction liquid, which was filtered through celite and the filter cake was rinsed with dichloromethane (500 mL*2). The filtrate was concentrated under reduced pressure and rotated till no fraction to give the crude product. The crude product was subjected to flash column chromatography for separation (silica gel mesh: 200-300, petroleum ether:ethyl acetate=10:1) to give the target compound 1-I.

$^1$H NMR (400 MHz, CHCl$_3$-d) δ ppm 7.51 (d, J=7.72 Hz, 1H) 7.42 (t, J=7.72 Hz, 1H) 7.19-7.23 (m, 1H) 5.08 (br t, J=6.84 Hz, 1H) 3.91 (br d, J=4.85 Hz, 2H) 1.90-2.07 (m, 2H) 1.63 (s, 3H) 1.55-1.61 (m, 2H) 1.53 (s, 3H) 0.86-0.97 (m, 9H) 0.59 (q, J=8.01 Hz, 6H).

Step 10: Synthesis of Compound 1-J

Compound 1-N (3.9 g, 17.55 mmol) and compound 1-I (7.27 g, 17.55 mmol) were added into 1,4-dioxane (60 mL), to which were then successively added potassium carbonate (3.37 g, 24.39 mmol), N,N'-dimethylethylenediamine (464.03 mg, 5.26 mmol, 566.58 μL) and copper iodide (501.26 mg, 2.63 mmol). The reaction system was purged with nitrogen three times and heated at 105° C. for 12 h with stirring under nitrogen atmosphere. After the reaction was completed, the reaction liquid was concentrated under reduced pressure and rotated till no fraction. Then 100 mL water, 80 mL of ethyl acetate for extraction and ammonia (5 mL 25%) were added and the reaction system was allowed to stand for liquid separation. The lower aqueous phase was extracted again with ethyl acetate (with 3 mL 25% ammonia added) (50 mL*1), and the two organic phases were combined. The organic phase was washed with water (80 mL*1) and saturated brine (100 mL*1) and was allowed to stand for liquid separation. The organic phase was concentrated under reduced pressure and rotated till no fraction to give the crude product. The crude product was subjected to flash column chromatography for separation (silica gel mesh: 100-200, eluent: petroleum ether:ethyl acetate=2:1) to give compound 1-J as light yellow oily liquid.

$^1$H NMR (400 MHz, CHCl$_3$-d) δ ppm 8.92 (s, 1H) 7.81-7.88 (m, 1H) 7.71 (d, J=8.07 Hz, 1H) 7.60 (d, J=7.70 Hz, 1H) 5.65 (ddt, J=16.87, 10.36, 6.19, 6.19 Hz, 1H) 5.10 (br t, J=6.91 Hz, 1H) 5.03 (d, J=10.27 Hz, 1H) 4.90 (s, 1H) 4.81-4.88 (m, 2H) 3.93 (d, J=5.26 Hz, 2H) 2.57 (s, 3H) 1.97-2.17 (m, 2H) 1.68-1.84 (m, 2H) 1.67 (s, 3H) 1.62 (s, 3H) 1.00 (t, J=7.89 Hz, 9H) 0.68 (q, J=8.03 Hz, 6H), MS-ESI m/z: 556.2[M+H]$^+$.

Step 11: Synthesis of Compound 1-K

Compound 1-J (8.38 g, 15.08 mmol) and barbituric acid (4.71 g, 30.15 mmol) were added into dichloromethane (100 mL), to which was then added tetrakis (triphenylphosphine) palladium (348.45 mg, 301.54 μμmol, 0.02 eq). The reaction system was purged with nitrogen three times and heated to 40° C. with stirring for 14 h. After the reaction was completed, to the reaction liquid was added with water (150 mL), which was allowed to stand for liquid separation. The upper aqueous phase was extracted again with dichloromethane (50 mL*1) and the two organic phases were combined. The organic phase was washed with saturated sodium bicarbonate solution (120 mL*1) and saturated brine (200 mL*1), dried over anhydrous sodium sulfate and filtered. The filtrate was concentrated under reduced pressure and rotated till no fraction to give the crude product. The crude product was subjected to flash column chromatography for separation (silica gel mesh: 200-300, petroleum ether:ethyl acetate=2:1-dichloromethane:methanol=70:1) to give the target compound 1-K.

$^1$H NMR (400 MHz, CHCl$_3$-d) δ ppm 8.95 (s, 1H) 8.34 (d, J=8.38 Hz, 1H) 7.86 (t, J=7.94 Hz, 1H) 7.55 (d, J=7.72 Hz, 1H) 5.24 (br t, J=7.06 Hz, 1H) 3.84-4.08 (m, 2H) 2.71 (s, 3H) 2.27-2.39 (m, 1H) 2.05 (s, 2H) 1.72-1.85 (m, 2H)

1.69 (s, 3H) 1.65 (s, 3H) 0.97-1.07 (m, 9H) 0.71 (q, J=8.01 Hz, 6H), MS-ESI m/z: 516.1 [M+H]⁺, MS-ESI m/z: 538.2 [M+Na]⁺.

Step 12: Synthesis of Compound 1-L

Compound 1-K (2.63 g, 5.10 mmol) and triphenylphosphine (1.74 g, 6.63 mmol) were added into tetrahydrofuran (85 mL), which was purged with nitrogen three times. Under nitrogen atmosphere, the reaction system was cooled to 0° C. with ice-salt bath, to which was added dropwise slowly diisopropyl azodicarboxylate (1.34 g, 6.63 mmol, 1.29 mL) with the temperature maintained 0° C.-5° C. After addition, the reaction system returned to 20° C. with stirring for 12 h. After the reaction was completed, to the reaction liquid was added water (100 mL) and the solvent was removed under reduced pressure. To the reaction system was then added water (100 mL), which was extracted with ethyl acetate (80 mL*1). The organic phase was washed with saturated brine (100 mL*1) and was concentrated under reduced pressure and rotated till no fraction to give the crude product. The crude product was subjected to flash column chromatography for separation (silica gel mesh: 100-200, eluent: petroleum ether:ethyl acetate:dichloromethane=4:1:0.2) to give the target compound 1-L.

¹H NMR (400 MHz, CHCl₃-d) δ ppm 8.97 (s, 1H) 7.75-7.84 (m, 1H) 7.55-7.72 (m, 2H) 4.97 (td, J=12.51, 6.50 Hz, 1H) 4.88 (br s, 1H) 2.58 (s, 3H) 1.92-2.03 (m, 2H) 1.77 (s, 3H) 1.53-1.69 (m, 1H) 1.33-1.50 (m, 2H) 1.26 (d, J=6.17 Hz, 4H) 0.99 (t, J=7.94 Hz, 9H) 0.67 (q, J=7.94 Hz, 6H), MS-ESI m/z: 498.0[M+H]⁺.

Step 13: Synthesis of Compound 1-M

Compound 1-L (1.02 g, 2.05 mmol) was added into tetrahydrofuran (6 mL) and then tetrabutyl ammonium fluoride (1 M, 4.10 mL) was added into the reaction system, which was heated to 45° C. with stirring for 2.5 h. After the reaction was completed, the reaction liquid was added into water (30 mL), which was extracted with ethyl acetate (10 mL*1). The organic phase was concentrated under reduced pressure and rotated till no fraction to give the crude product. The crude product was subjected to flash column chromatography for separation (silica gel mesh: 100-200, petroleum ether:ethyl acetate=3:1-2:1) to give compound 1-M.

¹H NMR (400 MHz, DMSO-d₆) δ ppm 9.02 (s, 1H) 7.96 (t, J=7.94 Hz, 1H) 7.66 (br s, 2H) 5.33-5.39 (m, 1H) 4.83 (br s, 1H) 4.71 (br d, J=14.33 Hz, 1H) 2.53 (s, 3H) 1.99 (s, 1H) 1.89 (br d, J=16.32 Hz, 1H) 1.61 (s, 3H) 1.21-1.39 (m, 3H), MS-ESI m/z: 383.9[M+H]⁺.

Step 14: Synthesis of Compound 1

Compound 1-L (0.175 g, 456.36 µmol) was dissolved in dichloromethane (3.5 mL), to which was then added meta-chloroperbenzoic acid (147.66 mg, 684.54 µmol, 80% purity). The reaction system was stirred at 20° C. for 2 h. After detection, N,N-diisopropylethylamine (147.45 mg, 1.14 mmol, 198.72 µL) and compound 4-(4-methylpiperazino) aniline (96.02 mg, 502.00 µmol) were added slowly into the reaction system, which was heated to 40° C. with stirring for 12 h. After the reaction was completed, the reaction liquid was added into saturated sodium sulfite solution (3 mL) with stirring for 10 min, and then sodium hydroxide solution (4 mL, 3N) was added with stirring for 10 min. Dichloromethane (10 mL*3) was added for extraction. The organic phases were combined and washed with water (25 mL*1) and saturated brine (20 mL*2), and were allowed to stand for liquid separation. The organic phase was concentrated under reduced pressure and rotated till no fraction to give the crude product. The crude product was subjected to preparative Liquid Chromatograph for separation (chiral column: Waters Xbridge BEH C18 100*30 mm*10 µm; mobile phase: [H₂O (0.04% NH₃H₂O+10 mM NH₄HCO₃)-ACN]; ACN %: 20%-50%, 10 min) to give crude compound 1. The crude compound 1 was resolved with SFC (chiral column: DAICEL CHIRALPAK AD (250 mm*30 mm, 10 µm); mobile phase: [0.1% NH₃H₂O MeOH]; MeOH %: 60%-60%, 15 min) to give the target compound 1 (retention time: 6.02 min).

¹H NMR (400 MHz, CHCl₃-d) δ ppm 8.85 (s, 1H) 7.81 (br t, J=7.61 Hz, 2H) 7.47 (br d, J=8.82 Hz, 2H) 7.21-7.31 (m, 1H) 6.91 (br d, J=8.60 Hz, 2H) 5.52 (br s, 1H) 4.21-5.12 (m, 2H) 3.13-3.27 (m, 4H) 2.54-2.65 (m, 4H) 2.37 (s, 3H) 1.99-2.12 (m, 1H) 1.80-1.99 (m, 3H) 1.70 (s, 4H). MS-ESI m z: 527.2[M+H]⁺.

Example 2: Compound 2

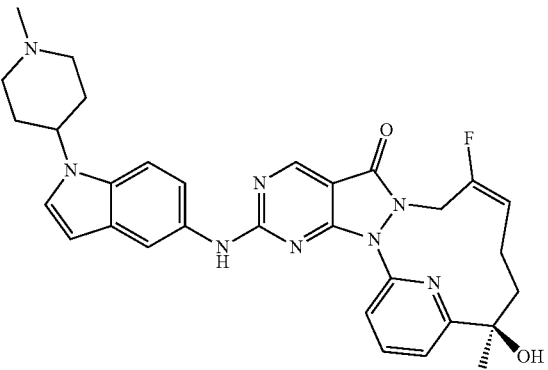

Synthesis Scheme:

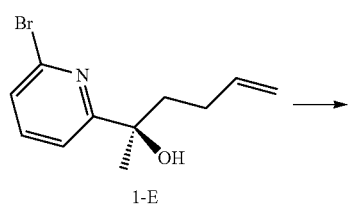

1-E

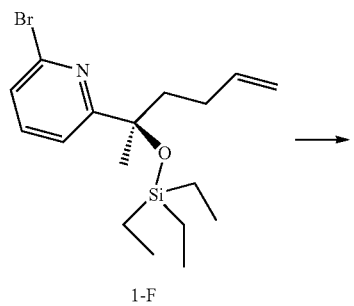

1-F

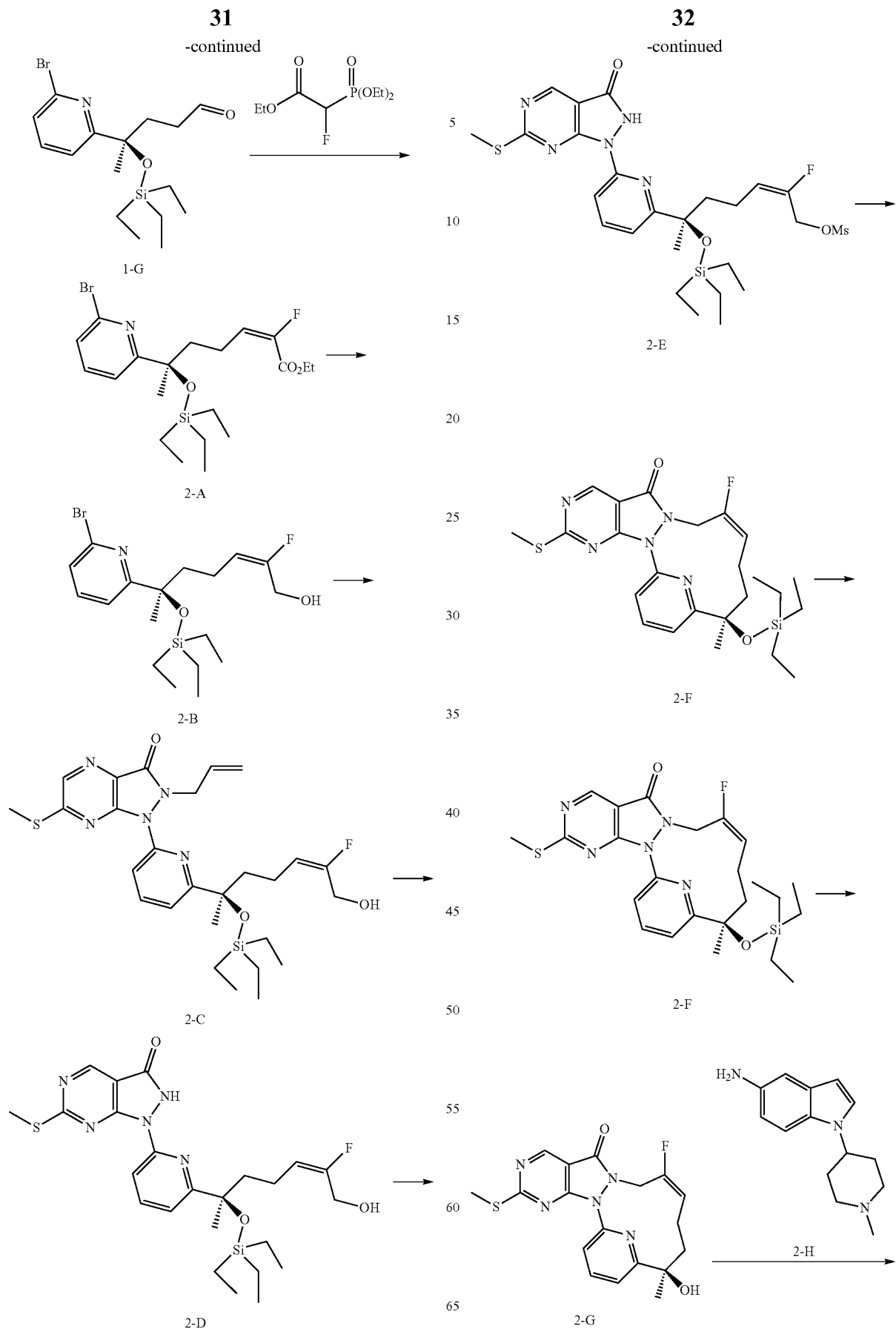

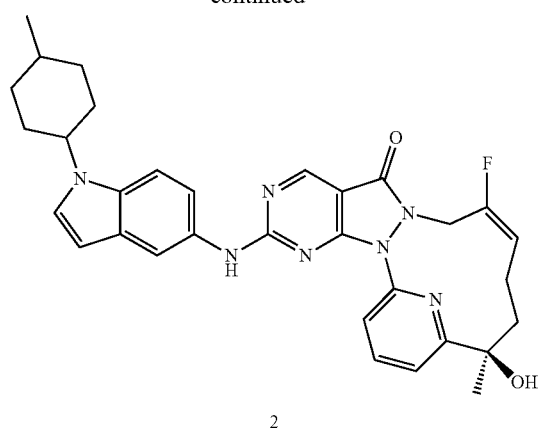

2

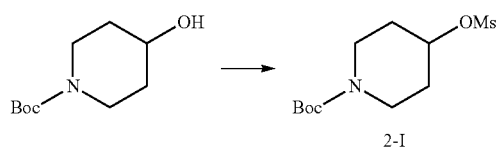

2-I

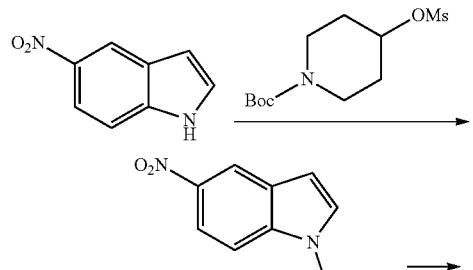

2-J

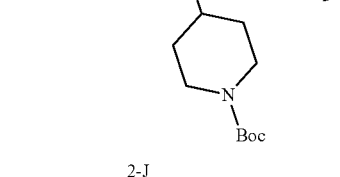

2-K

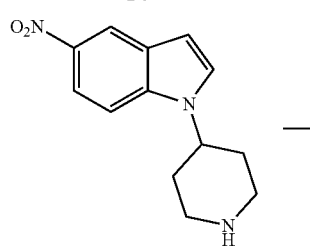

2-L

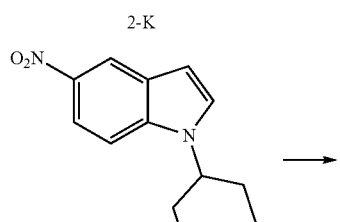

2-H

Step 1: Synthesis of Compound 2-I

Compound N-tert-Butoxycarbonyl-4-hydroxypiperidine (10 g, 49.69 mmol) was added to dichloromethane (200 mL) with the temperature maintained 0° C.-5° C. Triethylamine (7.54 g, 74.53 mmol, 10.37 mL) and methanesulfonyl chloride (6.89 g, 60.12 mmol, 4.65 mL) were added and the reaction system was stirred under controlled temperature for 3 h. After the reaction was completed, the reaction liquid was added into citric acid solution (180 mL, 5%) and was allowed to stand for liquid separation. The organic phase was washed successively with saturated sodium bicarbonate solution (150 mL) and saturated brine (150 mL), dried over anhydrous sodium sulfate and then filtered. The filtrate was concentrated under reduced pressure and rotated till no fraction to give target compound 2-I.

$^1$H NMR (400 MHz, CHCl$_3$-d) δ ppm 4.88 (tt, J=7.75, 3.72 Hz, 1H) 3.64-3.76 (m, 2H) 3.24-3.36 (m, 2H) 3.04 (s, 3H) 1.90-2.02 (m, 2H) 1.76-1.88 (m, 2H) 1.46 (s, 9H).

Step 2: Synthesis of Compound 2-J

Compound 5-nitroindole (6 g, 37.00 mmol) was added into N,N-dimethylformamide (60 mL), and sodium hydride (2.96 g, 74.01 mmol, 60% purity) was added into the reaction system at 0° C. with stirring for 1 h. Then compound 2-I (10.34 g, 37.00 mmol) was added into the reaction system, which was heated to 100° C. with stirring for 12 h. After the reaction was completed, the reaction system was added into water (200 mL) to quench the reaction. The reaction system was extracted with ethyl acetate (50 mL*3) and the organic phase was washed with diluted sodium hydroxide solution (150 mL) once and then saturated brine (150 mL) once. The organic phase was concentrated under reduced pressure and rotated to dryness to give the target compound 2-J, which was used directly for the next step. (MS-ESI m/z: 245.9)

Step 3: Synthesis of Compound 2-K

Compound 2-J (12.90 g, 37.35 mmol) was added into ethyl acetate (100 mL), and then hydrochloride/ethyl acetate (4 M, 80 mL) was added into the reaction system which was stirred at 20° C. for 2 h. After the reaction was completed, the reaction liquid was rotated under reduced pressure to remove hydrochloric acid gas and then filtered. The filter cake was rinsed with ethyl acetate (20 mL) once and was concentrated under reduced pressure and rotated till no fraction to give the target compound 2-K, which was used directly for the next step.

Step 4: Synthesis of Compound 2-L

At 20° C., compound 2-K (4.59 g, 18.71 mmol) was added into dichloromethane (90 mL) and formaldehyde solution (3.04 g, 37.43 mmol, 2.79 mL, 37% purity) and triethylamine (3.79 g, 37.43 mmol, 5.21 mL) were added slowly into the reaction system. After stirring for 5 min, acetic acid (3.5 mL) was added with stirring at 20° C. for 1 h and then sodium cyanoborohydride (3.53 g, 56.14 mmol)

was added with stirring for 2 h. After the reaction was completed, the reaction liquid was cooled with ice water, to which was slowly added sodium hydroxide solution (50 mL, 1M) to quench the reaction, and then water (150 mL) was added for dilution. The reaction system was allowed to stand for liquid separation. The dichloromethane organic phase was washed again with saturated brine (100 mL). The organic phase was concentrated under reduced pressure and rotated till no fraction to give crude product. The crude product was subjected to flash column chromatography for separation (silica gel mesh: 100-200, eluent: dichloromethane:methanol=40:1) to give target compound 2-L.

$^1$H NMR (400 MHz, $CH_3OH$-$d_4$) δ ppm 8.53 (d, J=2.20 Hz, 1H) 8.06 (dd, J=9.15, 2.09 Hz, 1H) 7.61 (d, J=9.04 Hz, 1H) 7.58 (d, J=3.53 Hz, 1H) 6.73 (d, J=3.31 Hz, 1H) 4.42-4.52 (m, 1H) 3.06 (br d, J=12.13 Hz, 2H) 2.38 (s, 3H) 2.29-2.36 (m, 2H) 2.00-2.18 (m, 4H). MS-ESI m/z: 260.0 $[M+H]^+$.

Step 5: Synthesis of Compound 2-H

Compound 2-L (1 g, 3.86 mmol) was added into methanol (35 mL) and ammonia (1 mL), and then palladium/carbon (0.6 g, 10% purity) was added. The reaction system was purged with hydrogen and stirred at 20° C. under hydrogen balloon for 12 h. After the reaction was completed, the reaction liquid was filtered with celite, rinsed with methanol (400 mL). The filtrate was concentrated under reduced pressure and rotated till no fraction to give the target compound 2-H.

$^1$H NMR (400 MHz, $CH_3OH$-$d_4$) δ ppm 7.24 (d, J=8.68 Hz, 1H) 7.20 (d, J=3.18 Hz, 1H) 6.94 (d, J=1.83 Hz, 1H) 6.72 (dd, J=8.62, 2.02 Hz, 1H) 6.26 (d, J=2.93 Hz, 1H) 4.18-4.29 (m, 1H) 3.02 (br d, J=12.10 Hz, 2H) 2.36 (s, 3H) 2.23-2.33 (m, 2H) 1.94-2.13 (m, 4H).

Step 6: Synthesis of Compound 1-F

Compound 1-E (50.00 g, 164.58 mmol) and 2,6-dimethylpyridine (21.16 g, 197.50 mmol, 23.00 mL) were added into dichloromethane (500 mL) and the reaction system was cooled to −10° C.-0° C. with dry ice. To the reaction system was slowly added triethylsilyl trifluoromethanesulfonate (52.21 g, 197.50 mmol, 44.62 mL, 1.2 eq), which was stirred at −10° C.-0° C. for 4 h. After detection, triethylsilyl trifluoromethanesulfonate (4.35 g, 16.46 mmol, 3.72 mL, 0.1 eq) was additionally added at −10° C.-0° C. with stirring for 12 h. After the reaction was completed, the reaction liquid was washed with saturated citric acid solution (500 mL*3) to give a solution of compound 1-F in dichloromethane, which was directly used for next step.

Step 7: Synthesis of Compound 1-G

A solution of compound 1-F as raw material in dichloromethane (500 mL) (calculated as 164.58 mmol) was cooled to −40° C. with dry ice ethanol bath, ozone was introduced under open state and the reaction was performed for 2.5 h. After the reaction was completed by detection, oxygen was introduced under open state for 45 min and then nitrogen was introduced under open state for 30 min. At −40° C., to the reaction system was slowly added triphenylphosphine (43.17 g, 164.58 mmol). After addition, the reaction system returned slowly to 20° C. and reaction was performed for 12 h. After the reaction was completed, the reaction liquid was concentrated under reduced pressure and rotated to dryness to give the crude product. The crude product was subjected to flash column chromatography for separation (silica gel mesh: 100-200, dichloromethane:petroleum ether=3:1 and petroleum ether:ethyl acetate=30:1-10:1) to give the target compound 1-G.

$^1$H NMR (400 MHz, $CHCl_3$-d) δ ppm 9.54-9.58 (m, 1H) 7.40-7.51 (m, 2H) 7.24 (dd, J=7.61, 0.99 Hz, 1H) 2.22-2.34 (m, 2H) 1.95-2.06 (m, 2H) 1.56-1.63 (m, 3H) 0.85-0.94 (m, 9H) 0.58 (q, J=8.01 Hz, 6H).

Step 8: Synthesis of Compound 2-A

Triethyl 2-fluoro-2-phosphonoacetate (9.73 g, 40.17 mmol, 8.18 mL) was dissolved in tetrahydrofuran (50 mL), which was cooled to −78° C. and n-butyllithium (2.5 M, 17.53 mL) was added dropwise. After addition, the reaction system was stirred for 30 min and a solution of 1-G (13.6 g, 36.52 mmol) in tetrahydrofuran (50 mL) was added dropwise. After addition, the reaction was performed at −78° C. for 1 h and TLC (dichloromethane:petroleum ether=1:1, $R_f$=0.3) confirmed completion of the reaction. 60 mL of saturated ammonium chloride solution was added dropwise into the reaction system to quench the reaction, which then returned to room temperature slowly and was subjected to liquid separation. The aqueous phase was extracted with 30 mL of ethyl acetate. The organic phases were combined, dried over anhydrous sodium sulfate, and then filtered and rotated to dryness to give compound 2-A as light yellow liquid, which was not purified and was used directly for the next step.

Step 9: Synthesis of Compound 2-B

Compound 2-A (19 g, 41.26 mmol) was dissolved in dichloromethane (150 mL) at 0° C., to which was added dropwise diisobutylaluminium hydride (1 M, 103.16 mL). After addition, the reaction was performed for 2 h at 0° C. and LCMS showed the reaction was completed. 60 mL of 10% potassium sodium tartrate solution was added into the reaction system, which was stirred for 30 min and then filtered. To the filtrate were added 150 mL of water and 150 mL of ethyl acetate for extraction. The organic phase was concentrated till no fraction to give compound 2-B as yellow and thick liquid. The crude product was used directly for next step without further purification.

Step 10: Synthesis of Compound 2-C

1-N (6.9 g, 31.04 mmol), compound 2-B (14.29 g, 34.15 mmol), N,N'-dimethylethylenediamine (820.97 mg, 9.31 mmol, 1.00 mL), potassium carbonate (10.73 g, 77.61 mmol) and CuI (886.84 mg, 4.66 mmol) were added into dioxane (150 mL), which was purged with nitrogen three times and warmed to 105° C. The reaction was performed for 15 h. The reaction system was cooled to room temperature and concentrated to remove the solvent, to which was added 200 mL of water and 20 mL of ammonia. The reaction system was extracted with 200 mL of ethyl acetate for liquid separation, and the aqueous phase was again extracted with 100 mL of ethyl acetate for liquid separation. The organic phases were combined, washed with 200 mL of water and 10 mL of ammonia, and then washed with 200 mL of water. The organic phase was dried over anhydrous sodium sulfate, then filtered and rotated to dryness. The crude product was subjected to column chromatography for purification (TLC: ethyl acetate:petroleum ether=1:1, Rf=0.4, eluent: ethyl acetate:petroleum ether=1:4) to give compound 2-C as yellow thick liquid.

Step 11: Synthesis of Compound 2-D

Compound 2-C (1 g, 1.79 mmol), ammonium formate (225.29 mg, 3.57 mmol) and [1,1'-Bis(diphenylphosphino)ferrocene]dichloropalladium (26.14 mg, 35.73 μmol) were added into dioxane (10 mL), which was purged with nitrogen three times and warmed to 100° C. The reaction was performed for 4 h.

Compound 2-C (1 g, 1.79 mmol,), ammonium formate (225.29 mg, 3.57 mmol) and [1,1'-Bis(diphenylphosphino)ferrocene]dichloropalladium (26.14 mg, 35.73 μmol) were added into dioxane (10 mL), which was purged with nitrogen three times and warmed to 60° C., and the reaction was performed for 1 h. The reaction was then warmed to 100° C. to be performed for 4 h.

The two reaction systems were rapidly cooled to room temperature with dry ice. With stirring, to the reaction system was added 100 mL of water and a large amount of solids precipitated which were subjected to suction filtration. The filter cake was rinsed with 20 mL of water to give brown solid. The solid was dissolved with 50 mL dichloromethane and subjected to flash silica gel column (TLC: methanol:dichloromethane=1:10, Rf=0.4, eluent: methanol:dichloromethane=1:20) to give compound 2-D as light yellow solid.

Step 12: Synthesis of Compound 2-E

Compound 2-D (2.5 g, 4.81 mmol) and triethylamine (1.46 g, 14.43 mmol, 2.01 mL) were added into dichloromethane (25 mL), and at 0° C., methanesulfonyl chloride (1.10 g, 9.62 mmol, 744.65 μL) was added. The reaction system returned to 20° C. and was stirred for 1.5 h. After the reaction was completed, the reaction was added into water (50 mL) and then dichloromethane (30 mL) was added for extraction. The reaction system was allowed to stand for liquid separation. The aqueous phase was extracted again with dichloromethane (30 mL) and the two organic phases were combined. The organic phase was washed again with saturated saline once (120 mL), dried over anhydrous sodium sulfate, and filtered. The filtrate was concentrated under reduced pressure till no faction to give compound 2-E, which was used directly for the next step.

Step 13: Synthesis of Compound 2-F

Compound 2-E (3.31 g, 5.54 mmol) was added into N,N-dimethylformamide (90 mL) and then potassium carbonate (1.99 g, 14.40 mmol) was added. The reaction system was heated to 50° C. with stirring for 12 h. After the reaction was completed, the reaction liquid was added into water (200 mL), and then ethyl acetate was added (250 mL*1) for extraction. The lower aqueous phase was extracted again with ethyl acetate (100 mL*1). The reaction system was allowed to stand for liquid separation. The two organic phases were combined, washed with semi-saturated brine (150 mL*2), dried over anhydrous sodium sulfate and then filtered. The filtrate was concentrated under reduced pressure and rotated till no fraction to give target compound 2-F. MS-ESI m/z: 502.2[M+H]$^+$.

Step 14: Synthesis of Compound 2-G

Compound 2-F (2.41 g, 4.80 mmol) was added into tetrahydrofuran (5 mL) and then tetrabutyl ammonium fluoride (1 M, 9.61 mL) was added. The reaction system was heated to 40° C. with stirring for 12 h. After the reaction was completed, to the reaction liquid was added water (20 mL), which was extracted with ethyl acetate (30 mL*2). Two organic phases were combined, washed with water once (50 mL), then washed with semi-saturated brine once (50 mL), dried over anhydrous sodium sulfate and filtered. The filtrate was concentrated under reduced pressure and rotated till no fraction to give the crude product. The crude product was subjected to medium pressure liquid chromatograph for separation (silica gel mesh: 100-200, ethyl acetate: petroleum ether=1:1) to give target compound 2-G.

$^1$H NMR (400 MHz, CHCl$_3$-d) δ ppm 8.98 (s, 1H) 7.89-7.97 (m, 1H) 7.84 (br d, J=7.95 Hz, 1H) 7.36 (d, J=7.58 Hz, 1H) 5.31 (s, 1H) 5.17-5.34 (m, 1H) 4.72-4.85 (m, 1H) 4.49-4.72 (m, 1H) 4.00 (s, 1H) 2.61 (s, 3H) 2.16-2.28 (m, 1H) 2.02-2.13 (m, 1H) 1.76-1.89 (m, 1H) 1.71 (s, 3H). MS-ESI m/z: 388.0[M+H]$^+$.

Step 15: Synthesis of Compound 2

At 19° C., compound 2-G (0.23 g, 593.65 μmol) was added into dichloromethane (3 mL), and then meta-chloroperbenzoic acid (192.08 mg, 890.48 μmol, 80% purity, 1.5 eq) was added. After stirring for 2 h, according to detection of reaction, the raw material points did not disappear completely. After meta-chloroperbenzoic acid (64.03 mg, 296.83 μmol, 80% purity) was additionally added, the reaction system was further stirred for 1 h and the reaction was detected. The raw material points disappeared and intermediate state occurred. N,N-diisopropylethylamine (191.81 mg, 1.48 mmol, 258.51 μL) and compound 2-H (136.14 mg, 593.65 μmol) were added successively and the reaction system was heated to 40° C. with stirring for 12 h. After the reaction was completed, the reaction was added into saturated sodium sulfite (7 ml) to quench the reaction. The reaction was stirred for 10 min and then sodium hydroxide solution (6 mL, 3M) was added. The reaction system was extracted with ethyl acetate (10 mL*3). The organic phases were combined, and washed with saturated brine (25 mL*2) and concentrated under reduced pressure and rotated till no fracture to give the crude product. The crude product was subjected to High Performance Liquid Chromatography for separation (chiral column: Waters Xbridge Prep OBD C18 150*40 mm*10 μm; mobile phase: [H$_2$O (10 mM NH$_4$HCO$_3$)-ACN]; ACN %: 30%-60%, 8 min) to give the target compound 2.

$^1$H NMR (400 MHz, CHCl$_3$-d) δ ppm 8.87 (br s, 1H) 7.96 (br d, J=7.82 Hz, 2H) 7.80-7.88 (m, 1H) 7.35 (d, J=8.80 Hz, 1H) 7.20-7.30 (m, 1H) 7.20-7.30 (m, 2H) 6.48 (d, J=2.93 Hz, 1H) 5.31 (s, 1H) 4.64-4.77 (m, 1H) 4.47 (br d, J=15.89 Hz, 1H) 4.16-4.28 (m, 1H) 4.07 (br s, 1H) 3.06 (br d, J=11.13 Hz, 2H) 2.39 (s, 3H) 2.02-2.28 (m, 1H) 2.02-2.28 (m, 7H) 1.73-1.86 (m, 2H) 1.66-1.72 (m, 3H). MS-ESI m/z: 569.3 [M+H]$^+$.

Example 3: Compound 3 and Compound 4

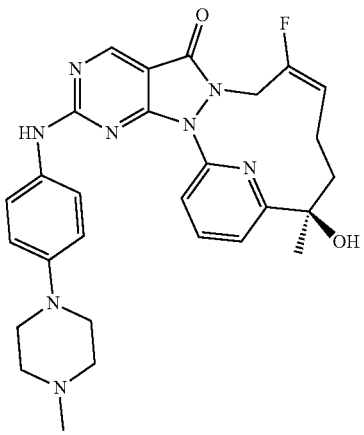

39
-continued
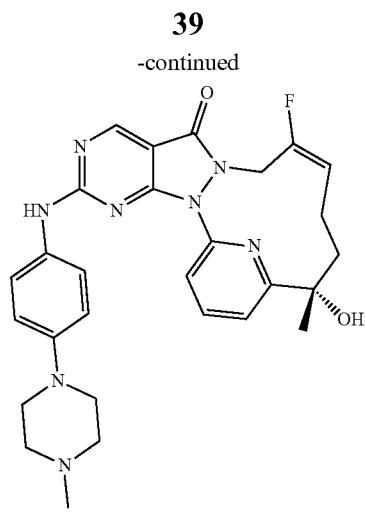
Synthesis Scheme:
40
-continued
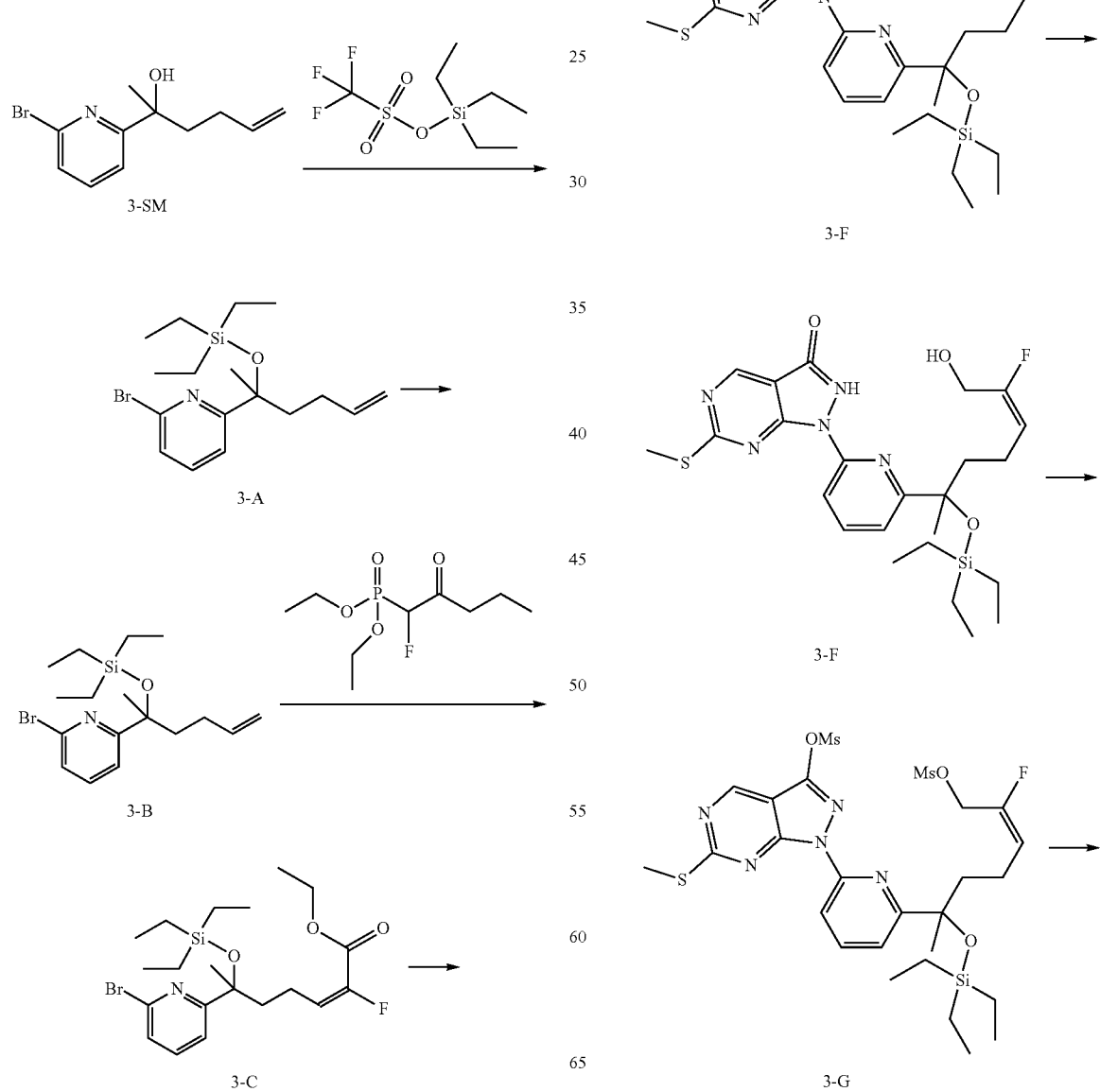

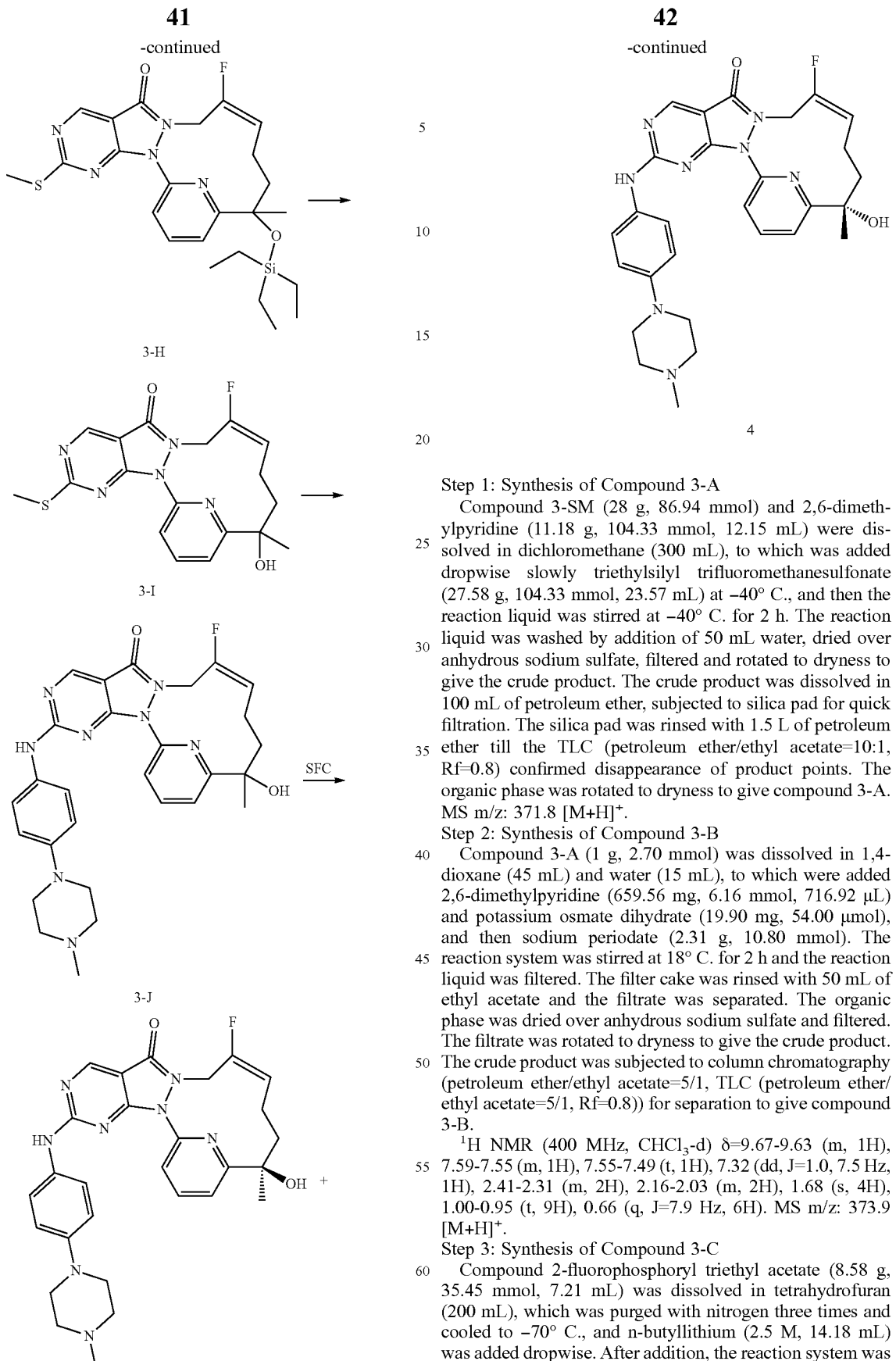

Step 1: Synthesis of Compound 3-A

Compound 3-SM (28 g, 86.94 mmol) and 2,6-dimethylpyridine (11.18 g, 104.33 mmol, 12.15 mL) were dissolved in dichloromethane (300 mL), to which was added dropwise slowly triethylsilyl trifluoromethanesulfonate (27.58 g, 104.33 mmol, 23.57 mL) at −40° C., and then the reaction liquid was stirred at −40° C. for 2 h. The reaction liquid was washed by addition of 50 mL water, dried over anhydrous sodium sulfate, filtered and rotated to dryness to give the crude product. The crude product was dissolved in 100 mL of petroleum ether, subjected to silica pad for quick filtration. The silica pad was rinsed with 1.5 L of petroleum ether till the TLC (petroleum ether/ethyl acetate=10:1, Rf=0.8) confirmed disappearance of product points. The organic phase was rotated to dryness to give compound 3-A. MS m/z: 371.8 [M+H]$^+$.

Step 2: Synthesis of Compound 3-B

Compound 3-A (1 g, 2.70 mmol) was dissolved in 1,4-dioxane (45 mL) and water (15 mL), to which were added 2,6-dimethylpyridine (659.56 mg, 6.16 mmol, 716.92 μL) and potassium osmate dihydrate (19.90 mg, 54.00 μmol), and then sodium periodate (2.31 g, 10.80 mmol). The reaction system was stirred at 18° C. for 2 h and the reaction liquid was filtered. The filter cake was rinsed with 50 mL of ethyl acetate and the filtrate was separated. The organic phase was dried over anhydrous sodium sulfate and filtered. The filtrate was rotated to dryness to give the crude product. The crude product was subjected to column chromatography (petroleum ether/ethyl acetate=5/1, TLC (petroleum ether/ethyl acetate=5/1, Rf=0.8)) for separation to give compound 3-B.

$^1$H NMR (400 MHz, CHCl$_3$-d) δ=9.67-9.63 (m, 1H), 7.59-7.55 (m, 1H), 7.55-7.49 (t, 1H), 7.32 (dd, J=1.0, 7.5 Hz, 1H), 2.41-2.31 (m, 2H), 2.16-2.03 (m, 2H), 1.68 (s, 4H), 1.00-0.95 (t, 9H), 0.66 (q, J=7.9 Hz, 6H). MS m/z: 373.9 [M+H]$^+$.

Step 3: Synthesis of Compound 3-C

Compound 2-fluorophosphoryl triethyl acetate (8.58 g, 35.45 mmol, 7.21 mL) was dissolved in tetrahydrofuran (200 mL), which was purged with nitrogen three times and cooled to −70° C., and n-butyllithium (2.5 M, 14.18 mL) was added dropwise. After addition, the reaction system was stirred for 30 min, and a solution of compound 3-B (11 g, 29.54 mmol) in tetrahydrofuran (50 mL) was added dropwise slowly. After addition, the reaction system was stirred for 2.5 h at −70° C. and then warmed slowly to 15° C. with stirring for 13 h. The reaction liquid was cooled to 0° C., to which was added slowly dropwise saturated ammonium chloride aqueous solution (100 mL). After addition, the reaction system was stirred for 20 min and subjected to liquid separation. The aqueous phase was extracted again with ethyl acetate (50 mL*3). The organic phases were combined, then washed with saturated brine (50 mL) once, dried over anhydrous sodium sulfate, filtered, and rotated to dryness to give compound 3-C. MS m/z: 460.1 $[M+H]^+$.

Step 4: Synthesis of Compound 3-D

Compound 3-C (14.03 g, 30.47 mmol) was dissolved in dichloromethane (150 mL), which was purged with nitrogen three times and cooled to 0° C. and diisobutylaluminium hydride (1 M, 76.18 mL) was added dropwise. After addition, the reaction system was stirred at 0° C. for 2 h, to which was added saturated potassium sodium tartrate aqueous solution (100 mL), where attention should be paid to significant gas releasing. After addition, the reaction system was stirred for 0.5 h to give colloidal suspension, which was filtered with celite. The filter cake was extracted with dichloromethane (50 mL*2). The organic phase was washed with saturated brine (100 mL), dried over anhydrous sodium sulfate, filtered and rotated to dryness to give compound 3-D.

$^1$H NMR (400 MHz, CHCl$_3$-d) δ=7.62-7.56 (d, 1H), 7.55-7.49 (t, 1H), 7.31 (d, J=7.6 Hz, 1H), 5.18-5.01 (m, 1H), 4.19-4.05 (m, 2H), 2.18-1.97 (m, 2H), 1.80-1.67 (m, 2H), 1.62 (s, 3H), 1.02-0.96 (t, 9H), 0.67 (q, J=7.8 Hz, 6H). MS m/z: 420.0 $[M+H]^+$.

Step 5: Synthesis of Compound 3-E

Compound 1-N (6.84 g, 30.79 mmol) was dissolved in 1,4-dioxane (200 mL), to which were added 3-D (11.71 g, 27.99 mmol), potassium carbonate (5.34 g, 38.62 mmol), copper iodide (5.33 g, 27.99 mmol) and N,N-dimethylethylenediamine (2.76 g, 31.34 mmol, 3.37 mL). The reaction system was purged with nitrogen three times and stirred at 105° C. for 12 h. The reaction system was added 50 mL of ammonia, and was extracted with ethyl acetate (50 mL*3). The organic phases were combined and washed with saturated brine (50 mL) once, dried over anhydrous sodium sulfate and filtered. The filtrate was rotated to dryness to give the crude product. The crude product was subjected to column chromatography (petroleum ether/ethyl acetate=2/1, TLC (petroleum ether/ethyl acetate=2/1, Rf=0.4)) for separation to give compound 3-E.

$^1$H NMR (400 MHz, CHCl$_3$-d) δ=8.93 (s, 1H), 7.86 (t, J=7.9 Hz, 1H), 7.73 (dd, J=0.8, 8.0 Hz, 1H), 7.60 (d, J=7.5 Hz, 1H), 5.65 (m, 1H), 5.08-4.97 (m, 2H), 4.91-4.76 (m, 3H), 4.05 (d, J=6.3 Hz, 1H), 4.02-3.98 (d, 1H), 2.58 (s, 3H), 2.12-2.05 (m, 2H), 1.79-1.70 (m, 2H), 1.63 (s, 3H), 1.61 (s, 1H), 1.02-0.97 (t, 9H), 0.68 (q, J=8.0 Hz, 6H). MS m/z: 560.2 $[M+H]^+$.

Step 6: Synthesis of Compound 3-F

Compound 3-E (9.94 g, 17.76 mmol) was dissolved in 1,4-dioxane (100 mL), and ammonium formate (2.24 g, 35.51 mmol) and 1,1-bis(diphenylphosphino)ferrocene]dichloropalladium (649.66 mg, 887.87 μmol) were added. The reaction system was purged with nitrogen three times and stirred at 100° C. for 4 h. The reaction system was extracted with addition of 150 mL of water and dichloromethane (100 mL*2). The organic phases were combined and washed with addition of saturated brine (100 mL*2), dried over anhydrous sodium sulfate, filtered and rotated to dryness to give compound 3-F. MS m/z: 520.1 $[M+H]^+$.

Step 7: Synthesis of Compound 3-G

Compound 3-F (8.5 g, 16.36 mmol) was dissolved in dichloromethane (100 mL) and triethylamine (4.97 g, 49.07 mmol) was added. At 0° C., methanesulfonyl chloride (4.33 g, 37.80 mmol, 2.93 mL) was slowly added and then the reaction system was stirred at 15° C. for 2 h. 30 mL of water was added slowly to quench the reaction and liquid separation was performed. The aqueous phase was extracted with dichloromethane (15 mL*2). The organic phases were combined, washed with addition of 30 mL of saturated brine, dried over anhydrous sodium sulfate, filtered and rotated to dryness to give compound 3-G. MS m/z: 676.1 $[M+H]^+$.

Step 8: Synthesis of Compound 3-H

Compound 3-G (10.4 g, 15.39 mmol) was dissolved in N,N-dimethylformamide (250 mL), and potassium carbonate (5.53 g, 40.01 mmol) was added. The reaction system was stirred at 50° C. for 5 h and extracted with addition of 500 mL of water and ethyl acetate (50 mL*3). The organic phase was again washed with 500 mL of water once and saturated brine (50 mL) once, dried over anhydrous sodium sulfate, filtered and rotated to dryness to give compound 3-H. MS m/z: 502.0 $[M+H]^+$.

Step 9: Synthesis of Compound 3-I

Compound 3-H (8.74 g, 17.42 mmol) was dissolved tetrahydrofuran (100 mL) and tetrabutyl ammonium fluoride (1 M, 17.42 mL) was added. The reaction system was stirred at 20° C. for 24 h and the reaction liquid was rotated to dryness, which was dissolved with addition of dichloromethane (50 mL), washed with water (30 mL*2), then with saturated brine (30 mL) once, dried over anhydrous sodium sulfate, filtered and rotated to dryness to give the crude product. The crude product was subjected to column chromatography (ethyl acetate/petroleum ether=1/1, 3/1, 4/1, TLC (ethyl acetate/petroleum ether=3/1, Rf=0.4)) for separation to give 3-I.

Step 10: Synthesis of Compound 3-J

Compound 3-I (1.1 g, 2.84 mmol) was dissolved in dichloromethane (30 mL), and meta-chloroperbenzoic acid (734.93 mg, 3.41 mmol, 80% purity) was added. The reaction system was stirred at 30° C. for 1 h, to which were added N,N-diisopropylethylamine (917.37 mg, 7.1 mmol) and 4-(4-methylpiperazino) aniline (597.37 mg, 3.12 mmol), and then stirred at 50° C. for 12 h. To the reaction liquid was added 10 mL of saturated sodium carbonate solution, which was stirred for 10 min, and extracted with ethyl acetate (15 mL*3). The organic phases were combined, washed with saturated sodium sulfite solution (20 mL) once, then washed with saturated brine (20 mL) once, dried over anhydrous sodium sulfate, filtered and rotated to dryness to give the crude product. The crude product was subjected to column chromatography (dichloromethane/methanol=10/1, TLC (dichloromethane/methanol=10/1, Rf=0.3)) for separation to give solid. The solid was dissolved with addition of 5 mL methanol and solid precipitated, which was stirred for 2 h and filtered. The filter cake was rotated to dryness to give compound 3-J. MS m/z: 531.1 $[M+H]^+$.

Step 11: Synthesis of Compound 3 and Compound 4

Compound 3-J was subjected to SFC chiral resolution (chromatographic column: DAICEL CHIRALPAK AD 250 mm*30 mm diameter, 10 μm; mobile phase: A: supercritical $CO_2$, B: ETOH (0.1% $NH_3H_2O$), A:B=55:45 at 70 mL/min, to give 3, retention time: 9.1 min. $^1$H NMR (400 MHz, CHCl$_3$-d) δ=8.90-8.83 (s, 1H), 7.90-7.82 (d, 2H), 7.78-7.54 (m, 1H), 7.47 (d, J=9.0 Hz, 2H), 7.32-7.27 (m, 1H), 6.98-6.88 (d, 2H), 5.31 (m, 1H), 4.71 (t, J=15.3 Hz, 1H), 4.47 (m, 1H), 4.08 (s, 1H), 3.25-3.17 (m, 4H), 2.65-2.56 (m, 4H), 2.40-2.34 (s, 4H), 2.19 (m, 1H), 2.13-2.01 (m, 1H), 1.87-1.73 (m, 2H), 1.70 (s, 3H). MS m z: 531.0 [M+H]+. and 4, retention time: 11.8 min.
$^1$H NMR (400 MHz, CHCl$_3$-d) δ=8.87 (s, 1H), 7.87 (d, J=4.8 Hz, 2H), 7.47 (d, J=9.0 Hz, 2H), 7.33-7.28 (m, 1H), 6.94 (d, J=9.0 Hz, 2H), 5.38-5.28 (m, 1H), 4.78-4.65 (t, 2H), 4.57-4.38 (m, 1H), 4.06 (s, 1H), 3.27-3.16 (m, 6H), 2.65-2.56 (m, 4H), 2.38 (s, 3H), 2.22 (m, 1H), 2.13-2.03 (m, 1H), 1.85-1.72 (m, 2H), 1.70 (s, 3H) MS m z: 531.0 [M+H]+.
Example 4: Compound 5 and Compound 6
5
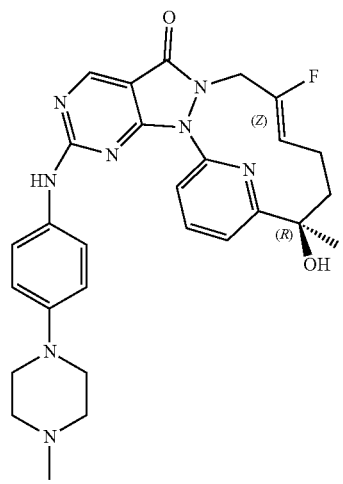
6
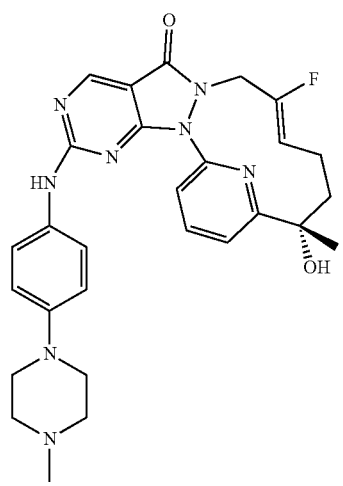
Synthesis Scheme:
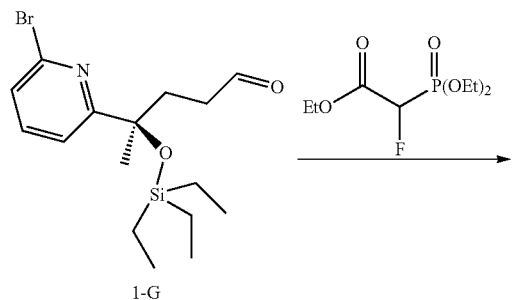
1-G
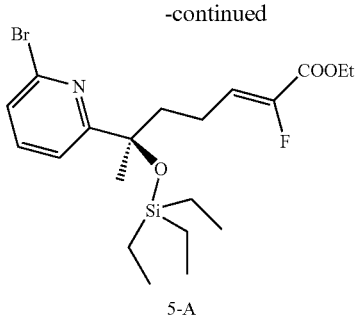
5-A
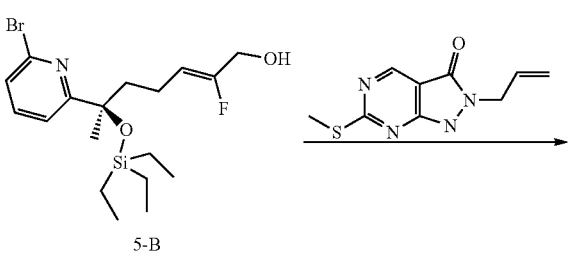
5-B
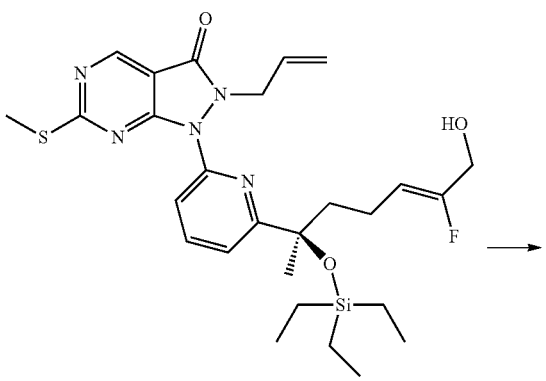
5-C
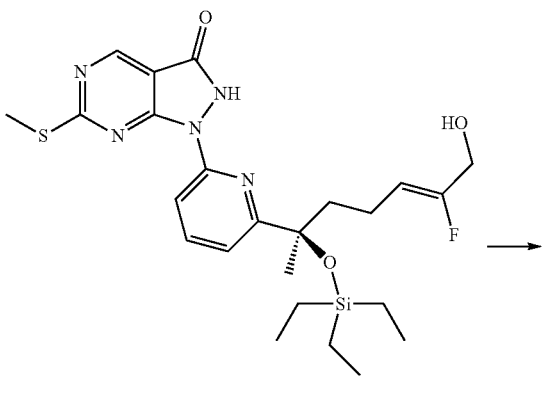
5-D

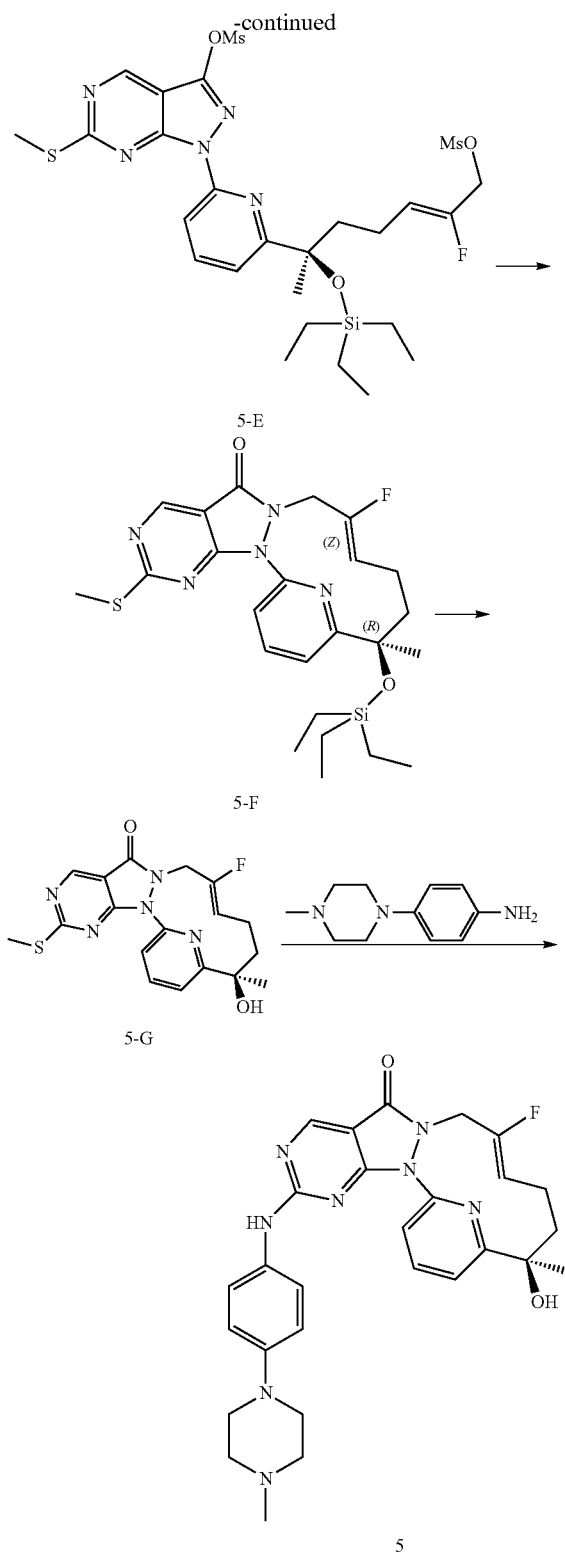

Step 1: Synthesis of Compound 5-A

An aqueous solution (0.36 mL) of the compound potassium carbonate (0.36 g, 2.60 mmol) was mixed with an aqueous solution (0.1 mL) of tetrabutylammonium bromide (0.1 g, 310.21 μmol), to which was added compound triethyl 2-fluoro-2-phosphonoacetate (78.05 mg, 322.26 μmol, 65.58 μL). After 15 min, compound 1-G (0.1 g, 268.55 μmol, 1 eq) was added at 15° C. with stirring for 16 h. Plate sampling confirmed completion of reaction. The reaction liquid was extracted with addition of petroleum ether/ethyl acetate=10:1 (50 mL*2). The organic phase was dried over anhydrous sodium sulfate, filtered and rotated to dryness. Purification with preparative thin layer chromatography to give compound 5-A. MS m/z: 460.0 [M+H]+.

Step 2: Synthesis of Compound 5-B

Compound 5-A (9.67 g, 21.00 mmol) was added into dichloromethane (100 mL), which was purged with nitrogen three times. At 0° C., to the reaction system was added slowly diisobutylaluminium hydride (1 M, 52.50 mL). After addition, the reaction system returned slowly from 0° C. to 19° C. with stirring for 12 h. The reaction liquid was added into 60 mL of saturated potassium sodium tartrate solution (the solution was in paste state) and then filtered with celite. The filter cake was rinsed with 1 L of dichloromethane in portions and the filtrate was concentrated under reduced pressure and rotated till no faction. 100 mL of water was added and extraction with dichloromethane was performed (70 mL*2). Two organic phases were combined, washed with 100 mL of saturated brine once, dried over anhydrous sodium sulfate and filtered. The filtrate was concentrated under reduced pressure and rotated till no fraction to give the crude product. The crude product was subjected to flash column chromatography (petroleum ether/ethyl acetate=5/1) go give compound 5-B.

Step 3: Synthesis of Compound 5-C

5-B (2.82 g, 6.75 mmol) was dissolved in dioxane (30 mL) and N,N'-dimethylethylenediamine (178.47 mg, 2.03 mmol, 217.91 μL), potassium carbonate (1.31 g, 9.45 mmol, 1.4 eq) and compound 1-N (1.5 g, 6.75 mmol) were added. The reaction system was purged with nitrogen three times and CuI (192.79 mg, 1.01 mmol) was added. The reaction system was warmed to 100° C. with stirring for 15 h. The reaction liquid was cooled and concentrated to remove most of the solvent. 50 mL of water, 5 mL of ammonia were added and extraction was performed with ethyl acetate (50 mL*2). The organic phases were combined, washed with water (50 mL), ammonia 1 mL, washed with 50 mL of saturated brine, dried over anhydrous sodium sulfate, filtered and rotated to dryness to give compound 5-C.

$^1$H NMR (400 MHz, CHCl$_3$-d) δ ppm 0.69 (q, J=8.01 Hz, 6H) 0.92-1.07 (m, 9H) 1.63 (s, 3H) 1.65-1.83 (m, 3H) 2.06-2.23 (m, 2H) 2.59 (s, 3H) 3.99 (dd, J=15.55, 6.28 Hz, 2H) 4.60 (t, J=7.28 Hz, 0.5H) 4.69 (t, J=7.28 Hz, 0.5H) 4.76-4.92 (m, 3H) 5.02 (d, J=10.14 Hz, 1H) 5.65 (ddt, J=16.87, 10.42, 6.09, 6.09 Hz, 1H) 7.63 (d, J=7.72 Hz, 1H) 7.70 (d, J=7.94 Hz, 1H) 7.82-7.90 (m, 1H) 8.93 (s, 1H).

Step 4: Synthesis of Compound 5-D

5-C (3 g, 5.36 mmol) was dissolved in dioxane (45 mL) and [1,1'-Bis(diphenylphosphino)ferrocene]dichloropalladium (196.07 mg, 267.97 μmol) and ammonium formate (675.88 mg, 10.72 mmol) were added. The reaction system was purged with nitrogen three times and heated to 100° C. with stirring for 4 h. The reaction liquid was cooled to 20° C., to which was added 50 mL of water with stirring for 10 min, and filtered. The filter cake was rotated to dryness. Dichloromethane (20 ml) was added with stirring for 10 min. Then filtration was performed, and the filter cake was rotated to dryness to give compound 5-D (1.87 g, 3.60 mmol).

$^1$H NMR (400 MHz, CHCl$_3$-d) δ ppm 0.72 (q, J=7.86 Hz, 6H) 0.89-1.11 (m, 9H) 1.53-1.69 (m, 1H) 1.71-1.80 (m, 3H) 1.85 (td, J=12.29, 4.08 Hz, 1H) 2.12-2.43 (m, 2H) 2.70 (s, 3H) 3.50 (s, 1H) 3.86-4.08 (m, 2H) 4.57-4.80 (m, 1H) 7.56 (d, J=7.72 Hz, 1H) 7.85 (t, J=7.94 Hz, 1H) 8.35 (d, J=8.16 Hz, 1H) 8.95 (s, 1H).

Step 5: Synthesis of Compound 5-E

Compound 5-D (1.67 g, 3.21 mmol) was dissolved in dichloromethane (50 mL) and triethylamine (975.48 mg, 9.64 mmol, 1.34 mL) was added. The reaction system was cooled to 0° C. and methanesulfonyl chloride (736.18 mg, 6.43 mmol, 497.42 μL) was added dropwise. After addition, the reaction system was stirred for 1 h. 30 mL of water was slowly added to quench the reaction and liquid separation was performed. The aqueous phase was extracted with dichloromethane (15 mL). The organic phases were combined, washed with 50 mL of saturated brine, dried over anhydrous sodium sulfate, filtered and rotated to dryness to give compound 5-E (crude) as yellow oil.

Step 6: Synthesis of Compound 5-F

Compound 5-E (2.17 g, 3.21 mmol) was dissolved in N,N-dimethylformamide (65 mL) and potassium carbonate (1.15 g, 8.35 mmol) was added. The reaction system was warmed to 80° C. with stirring for 3 h. The reaction liquid was cooled and concentrated under reduced pressure to remove most of the solvent and water (100 mL) was added. The aqueous phase was extracted with ethyl acetate (50 mL*2). The organic phases were combined, washed with saturated brine (100 mL), dried over anhydrous sodium sulfate, filtered and rotated to dryness. Silica gel column purification was performed with eluent polarity of petroleum ether:ethyl acetate=3:1 to give 5-F (0.4 g, 797.30 μmol,).

$^1$H NMR (400 MHz, CHCl$_3$-d) δ ppm 0.65 (q, J=8.09 Hz, 6H) 0.98 (t, J=7.83 Hz, 9H) 1.68 (s, 3H) 1.69-1.76 (m, 1H) 1.85 (br d, J=11.91 Hz, 1H) 2.24 (br d, J=13.89 Hz, 1H) 2.55 (s, 3H) 2.62-2.77 (m, 1H) 3.48-3.67 (m, 1H) 3.69-3.86 (m, 1H) 5.19 (br d, J=15.44 Hz, 1H) 7.52 (d, J=7.72 Hz, 1H) 7.75 (d, J=7.28 Hz, 1H) 7.85-7.90 (m, 1H) 8.94 (s, 1H).

Step 7: Synthesis of Compound 5-G

Compound 5-E (350 mg, 697.64 μmol) was dissolved in tetrahydrofuran (2 mL) and tetrabutylammonium bromide (1 M, 2.09 mL, 3 eq) was added. After addition, the reaction was warmed to 40° C. with stirring for 1 h. The reaction was extracted with 15 mL of water, ethyl acetate (20 mL). The organic phase was washed with saturated brine (20 mL*2), dried over anhydrous sodium sulfate, filtered and rotated to dryness to give compound 5-G.

$^1$H NMR (400 MHz, CHCl$_3$-d) δ ppm 1.56 (td, J=13.51, 3.64 Hz, 2H) 1.64-1.70 (m, 3H) 1.77 (br dd, J=14.00, 3.20 Hz, 1H) 2.01-2.12 (m, 1H) 2.56 (s, 3H) 3.00-3.14 (m, 1H) 3.49-3.67 (m, 1H) 3.81-3.96 (m, 1H) 4.59 (d, J=3.09 Hz, 1H) 5.25 (br d, J=15.66 Hz, 1H) 7.32 (d, J=7.72 Hz, 1H) 7.62 (d, J=7.94 Hz, 1H) 7.90-7.97 (m, 1H) 8.96 (s, 1H).

Step 8: Synthesis of Compound 5 and Compound 6

Compound 5-G (0.3 g, 774.33 μmol) was dissolved in dichloromethane (10 mL) and meta-chloroperbenzoic acid (235.81 mg, 1.16 mmol, 85% purity) was added at 15° C. with stirring for 0.5 h. N,N-diisopropylethylamine (200.15 mg, 1.55 mmol, 269.74 μL, 2 eq) and compound 4-(4-methylpiperazino) aniline (162.92 mg, 851.77 μmol) were added and reaction system was stirred at 15° C. for 15 h. 15 mL of saturated sodium sulfite solution and 3N aqueous sodium hydroxide solution were added and the reaction system was stirred for 0.5 h and extracted. The aqueous phase was extracted with dichloromethane (10 mL). The organic phases were combined, washed with saturated brine (20 mL*2), dried over anhydrous sodium sulfate, filtered and rotated to dryness. 5 mL of methanol was added and stirring was performed for 0.5 h followed by filtration. The filter cake was washed with methanol (2 mL*2) and rotated under reduced pressure to dryness. SFC purification (chiral column: DAICEL CHIRALPAK AD (250 mm*30 mm, 10 μm); mobile phase: [0.1% NH$_3$H$_2$O IPA]; IPA %: 50%-50%, 10 min) was performed to give 5 (retention time: 9.61 min).

$^1$H NMR (400 MHz, CHCl$_3$-d) δ ppm 1.52-1.55 (m, 1H) 1.67 (s, 3H) 1.74-1.78 (m, 1H) 2.04-2.08 (m, 1H) 2.37 (s, 3H) 2.58-2.60 (m, 4H) 3.09-3.18 (m, 1H) 3.18-3.21 (m, 4H) 3.48-3.60 (m, 1H) 3.93-3.95 (m, 1H) 4.65 (br d, J=3.2 Hz, 2H) 5.18-5.22 (m, 1H) 6.90 (d, J=8.8 Hz, 2H) 7.26 (m, 1H) 7.44 (br d, J=8.8 Hz, 2H) 7.59-7.61 (m, 1H) 7.85-7.91 (m, 1H) 8.84 (s, 1H).

MS m/z: 531.2 [M+H]$^+$.

Biological Test

Experimental Example 1: In Vitro Enzyme Inhibitory Activity of the Present Compounds The compounds used for experiments were all prepared in-house, and their chemical names and structural formulas were shown in the preparation examples for each compound. The experimental tests were carried out in Eurofins, which provided the experimental results.

In the Wee1 reaction system, 20 mM Tris-HCl, pH 8.5, 0.2 mM EDTA, 500 μM polypeptide substrate (LSN-LYHQGKFLQTFCGSPLYRRR) (Sequence ID No. 1), 10 mM magnesium acetate and a certain concentration of [8-33P]-ATP (intensity of about 500 cpm/pmol) were added. Addition of Mg$^{2+}$ and ATP mixed solution initiated the reaction. Incubation was performed at room temperature for 40 min and 3% phosphate buffer was added to terminate the reaction. 10 μL of the reaction solution was filtered on a continuous filter P30, and washed with 75 mM phosphate buffer three times, and washed with methanol once, 5 min for each time. After drying, the scintillation counting was used to read the values.

TABLE 1

| In vitro enzymatic activity test results of the present compounds (IC$_{50}$) | |
|---|---|
| No. | Wee1 (IC$_{50}$ nM) |
| 1 | 130 |
| 2 | 37 |
| 3 | 28 |
| 4 | 110 |
| 5 | 43 |

Results:

It can be seen from Table 1 that the present compounds have good inhibitory effect on Wee1 kinase.

Experimental Example 2: In Vivo Pharmacodynamics Study of the Tested Drug on Human Pancreatic Cancer PC-07-0049 Subcutaneously Transplanted Tumor Model in Nude Mice Procedures: The selected experimental animals were BALB/c nude mice (6 animals per group), 6-8 weeks old, weigh 16-21 grams.

The establishment of the Human pancreatic carcinoma PC-07-0049 model was originally derived from surgically excised clinical samples, which was defined as the P0 generation after implantation in nude mice. The implantation of the tumor tissue of P0 generation into the next generation was defined as the P1 generation. The implantation was continued in nude mice in this way. The tumor of FP3 was revived through the P2 generation. The next generation generated by the FP3 generation was defined as FP4, and so on. The tumor tissue of the FP5 generation will be used for the drug efficacy test.

The PC-07-0049 FP5 tumor tissue was cut into small pieces (20-30 mm$^3$) after removing the necrotic tissue and was inoculated subcutaneously on the right back of each nude mouse. When the average tumor volume reached about 193 mm$^3$, according to the tumor volume, the animals were divided into random groups and administered.

The experimental index was to investigate whether tumor growth was inhibited, delayed or cured. The diameters of the tumors were measured with a vernier caliper twice a week. The tumor suppression efficacy of the compound was evaluated by TGI (%) or the relative tumor proliferation rate T/C (%). TGI (%) reflects the tumor growth inhibition rate.

Calculation of TGI (%): TGI (%)=[(1−(Average tumor volume at the end of a treatment group−average tumor volume at the beginning of the treatment group))/(Average tumor volume at the end of treatment in the solvent control group−the average tumor volume at the beginning of treatment in the solvent control group)]×100%.

The final experimental results were as follows:

TABLE 2

Tumor in vivo efficacy results in mouse

| Compound | TGI (%) |
|---|---|
| Gemcitabine (20 mg/kg twice per week) | 58% |
| Compound 3 in combination with gemcitabine (50 mg/kg once per day, 20 mg/kg twice per week) | 102% |

Conclusion: It can be seen from Table 2 that the combination of compound 3 and gemcitabine can significantly improve the inhibitory effect on mouse tumor.

$R_4$ is selected from the group consisting of $C_{3-8}$ cycloalkyl and 4-10 membered heterocycloalkyl, wherein the $C_{3-8}$ cycloalkyl and 4-10 membered heterocycloalkyl are optionally substituted by 1, 2 or 3 $R_c$;

$R_5$ is selected from the group consisting of H, F, Cl, Br, I, OH, $NH_2$, $C_{1-3}$ alkyl and $C_{1-3}$ alkoxy, wherein the $C_{1-3}$ alkyl is optionally substituted by 1, 2 or 3 $R_d$;

$R_a$ is each independently selected from the group consisting of F, Cl, Br, I, OH and $NH_2$;

$R_b$ is each independently selected from the group consisting of F, Cl, Br, I, OH and $NH_2$;

$R_c$ is each independently selected from the group consisting of H, F, Cl, Br, I, OH, $NH_2$ and $C_{1-3}$ alkyl, wherein the $NH_2$ is optionally substituted by 1 or 2 R, and the $C_{1-3}$ alkyl is optionally substituted by 1, 2 or 3 R;

$R_d$ is each independently selected from the group consisting of F, Cl, Br, I, OH and $NH_2$;

R is each independently selected from the group consisting of F, Cl, Br, I, OH and $NH_2$;

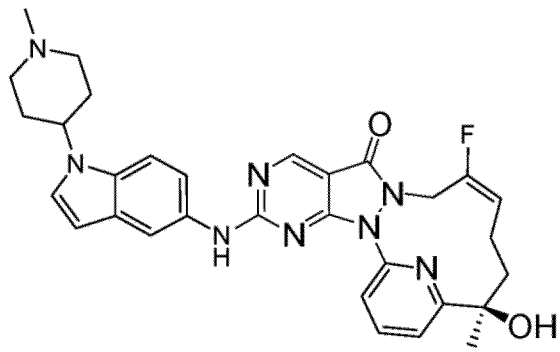

The invention claimed is:

1. A compound of formula (I), or a stereoisomer or a pharmaceutically acceptable salt thereof,

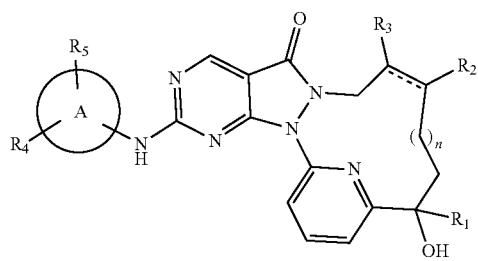

wherein,
⩘ is a single bond or a double bond;
n is 1, 2 or 3;
ring A is selected from the group consisting of $C_{6-10}$ aryl and 5-12 membered heteroaryl;
$R_1$ is selected from the group consisting of H and $C_{1-3}$ alkyl, wherein the $C_{1-3}$ alkyl is optionally substituted by 1, 2 or 3 $R_a$;
$R_2$ and $R_3$ are each independently selected from the group consisting of H, F, Cl, Br, I, OH, $NH_2$ and $C_{1-3}$ alkyl, wherein the $C_{1-3}$ alkyl is optionally substituted by 1, 2 or 3 $R_b$, and $R_2$ and $R_3$ are not H at the same time;

the 5-12 membered heteroaryl and 4-10 membered heterocycloalkyl contain 1, 2, 3 or 4 heteroatoms or heteroradicals independently selected from the group consisting of —NH—, O, —S— and N.

2. The compound according to claim 1, or a stereoisomer or a pharmaceutically acceptable salt thereof, wherein the ring A is selected from the group consisting of $C_{6-8}$ aryl and 5-10 membered heteroaryl.

3. The compound according to claim 1, or a stereoisomer or a pharmaceutically acceptable salt thereof, wherein the compound has the structure of formula (II) or (III)

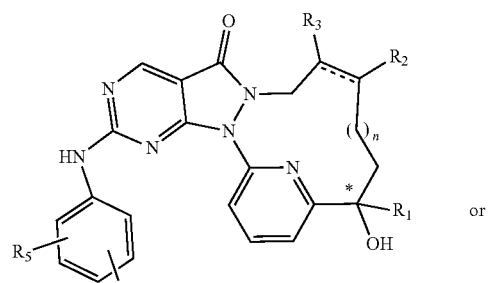

-continued (III)

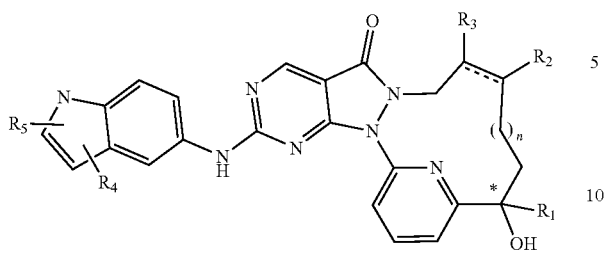

wherein,

⇌ is a single bond or a double bond;

n is 1, 2 or 3;

$R_1$ is each independently selected from the group consisting of H and $C_{1-3}$ alkyl, wherein the $C_{1-3}$ alkyl is optionally substituted by 1, 2 or 3 $R_a$;

$R_2$ and $R_3$ are each independently selected from the group consisting of H, F, Cl, Br, I, OH, $NH_2$ and $C_{1-3}$ alkyl, wherein the $C_{1-3}$ alkyl is optionally substituted by 1, 2 or 3 $R_b$, and $R_2$ and $R_3$ are not H at the same time;

$R_4$ is each independently selected from the group consisting of $C_{3-8}$ cycloalkyl and 4-10 membered heterocycloalkyl, wherein the $C_{3-8}$ cycloalkyl and 4-10 membered heterocycloalkyl are optionally substituted by 1, 2 or 3 $R_c$;

$R_5$ is each independently selected from the group consisting of H, F, Cl, Br, I, OH, $NH_2$, $C_{1-3}$ alkyl and $C_{1-3}$ alkoxy, wherein the $C_{1-3}$ alkyl is optionally substituted by 1, 2 or 3 $R_d$;

$R_a$ is each independently selected from the group consisting of F, Cl, Br, I, OH and $NH_2$;

$R_b$ is each independently selected from the group consisting of F, Cl, Br, I, OH and $NH_2$;

$R_c$ is each independently selected from the group consisting of H, F, Cl, Br, I, OH, $NH_2$ and $C_{1-3}$ alkyl, wherein the $NH_2$ is optionally substituted by 1 or 2 R, and the $C_{1-3}$ alkyl is optionally substituted by 1, 2 or 3 R;

$R_d$ is each independently selected from the group consisting of F, Cl, Br, I, OH and $NH_2$;

R is each independently selected from the group consisting of F, Cl, Br, I, OH and $NH_2$;

the 4-10 membered heterocycloalkyl contains 1, 2, 3 or 4 heteroatoms or heteroradicals independently selected from the group consisting of —NH—, O, —S— and N;

the carbon atom with "*" is a chiral carbon atom, which is present in a form of a single enantiomer as (R) or (S) or in a form enriched with an enantiomer.

4. The compound according to claim 3, or a stereoisomer or a pharmaceutically acceptable salt thereof, wherein the compound has the structure of formula (II-A) or (III-A):

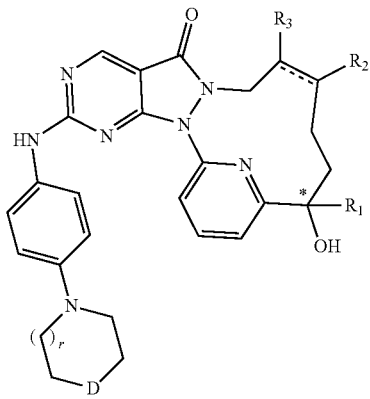

(II-A)

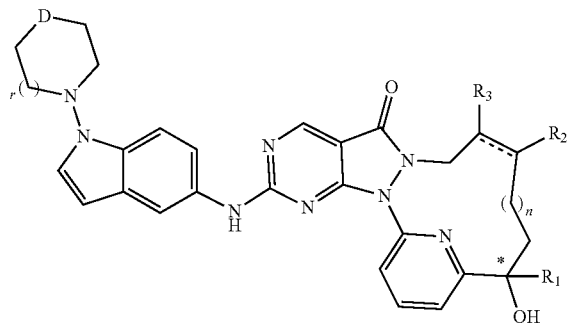

(III-A)

wherein, r is 1 or 2;

D is each independently selected from the group consisting of ×N($R_6$)— and —C($R_7$)($R_8$)—;

$R_6$ is each independently selected from the group consisting of H and $C_{1-3}$ alkyl, wherein the $C_{1-3}$ alkyl is optionally substituted by 1, 2 or 3 $R_e$;

$R_7$ and $R_8$ are each independently selected from the group consisting of H, F, Cl, Br, I, OH, $NH_2$ and $C_{1-3}$ alkyl, wherein the $NH_2$ is optionally substituted by 1 or 2 $R_f$, and the $C_{1-3}$ alkyl is optionally substituted by 1, 2 or 3 $R_f$;

$R_e$ is each independently selected from the group consisting of F, Cl, Br, I, OH and $NH_2$;

$R_f$ is each independently selected from the group consisting of F, Cl, Br, I, OH, $NH_2$ and $C_{1-3}$ alkyl;

the carbon atom with "*" is a chiral carbon atom, which is present in a form of a single enantiomer as (R) or (S) or in a form enriched with an enantiomer;

$R_1$ is each independently selected from the group consisting of H and $C_{1-3}$ alkyl, wherein the $C_{1-3}$ alkyl is optionally substituted by 1, 2 or 3 $R_a$;

$R_2$ and $R_3$ are each independently selected from the group consisting of H, F, Cl, Br, I, OH, $NH_2$ and $C_{1-3}$ alkyl, wherein the $C_{1-3}$ alkyl is optionally substituted by 1, 2 or 3 $R_b$, and $R_2$ and $R_3$ are not H at the same time;

$R_a$ is each independently selected from the group consisting of F, Cl, Br, I, OH and $NH_2$;

$R_b$ is each independently selected from the group consisting of F, Cl, Br, I, OH and $NH_2$.

5. The compound according to claim 1, or a stereoisomer or a pharmaceutically acceptable salt thereof, wherein $R_c$ is each independently selected from the group consisting of F, Cl, Br, I, OH, $NH_2$, $CH_3$ and Et.

6. The compound according to claim 4, or a stereoisomer or a pharmaceutically acceptable salt thereof, wherein $R_f$ is each independently selected from the group consisting of F, Cl, Br, I, OH, $NH_2$, $CH_3$ and Et.

7. The compound according to claim 1, or a stereoisomer or a pharmaceutically acceptable salt thereof, wherein $R_1$ is each independently selected from the group consisting of H, $CH_3$ and Et.

8. The compound according to claim 1, or a stereoisomer or a pharmaceutically acceptable salt thereof, wherein $R_2$ and $R_3$ are each independently selected from the group consisting of H, F, Cl, Br, I, OH, $NH_2$, $CH_3$ and Et, and $R_2$ and $R_3$ are not H at the same time.

9. The compound according to claim 1, or a stereoisomer or a pharmaceutically acceptable salt thereof, wherein $R_5$ is each independently selected from the group consisting of H, F, Cl, Br, I, OH, $NH_2$, $CH_3$, Et and $OCH_3$.

10. The compound according to claim 4, or a stereoisomer or a pharmaceutically acceptable salt thereof, wherein $R_6$ is each independently selected from the group consisting of H, $CH_3$ and Et.

11. The compound according to claim 4, or a stereoisomer or a pharmaceutically acceptable salt thereof, wherein $R_7$ and $R_8$ are each independently selected from the group consisting of H, F, Cl, Br, I, OH, $NH_2$, —$NH(CH_3)$, —$N(CH_3)_2$, $CH_3$ and Et.

12. The compound according to claim 11, or a stereoisomer or a pharmaceutically acceptable salt thereof, wherein $R_7$ is each independently selected from the group consisting of H, F, Cl, Br, I, OH, $NH_2$, —$NH(CH_3)$, —$N(CH_3)_2$, $CH_3$ and Et.

13. The compound according to claim 11, or a stereoisomer or a pharmaceutically acceptable salt thereof, wherein $R_8$ is each independently selected from the group consisting of H, F, Cl, Br, I, OH, $CH_3$ and Et.

14. The compound according to claim 4, or a stereoisomer or a pharmaceutically acceptable salt thereof, wherein the structural unit

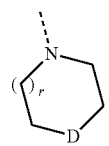

is selected from the group consisting of

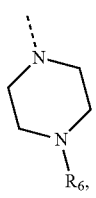 , 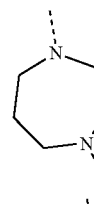 , 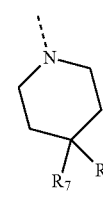 and

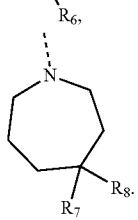

15. The compound according to claim 14, or a stereoisomer or a pharmaceutically acceptable salt thereof, wherein the structural unit

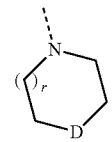

is selected from the group consisting of

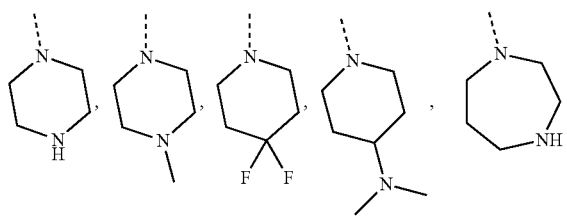

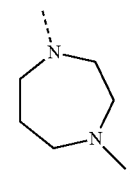 and .

16. The compound according to claim 1, or a stereoisomer or a pharmaceutically acceptable salt thereof, wherein the structural unit

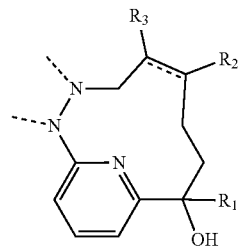

is selected from the group consisting of

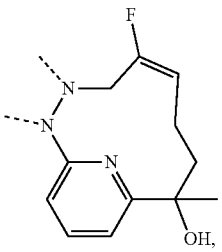 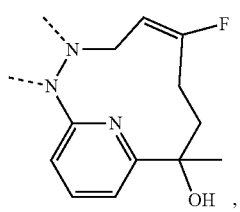

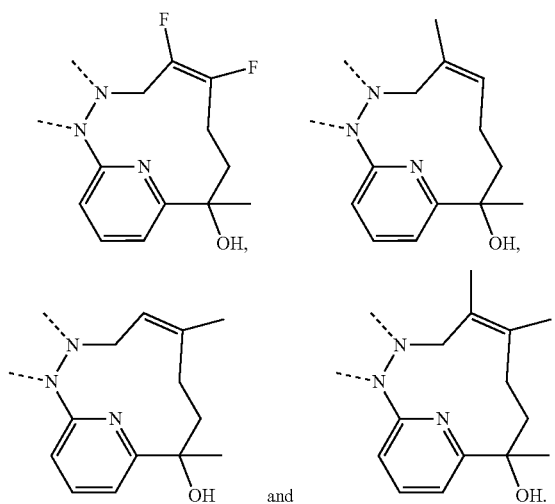

17. The compound according to claim 1, or a stereoisomer or a pharmaceutically acceptable salt thereof, wherein the compound has the structure of formula (II-A1), (II-A2) or (III-AA1)

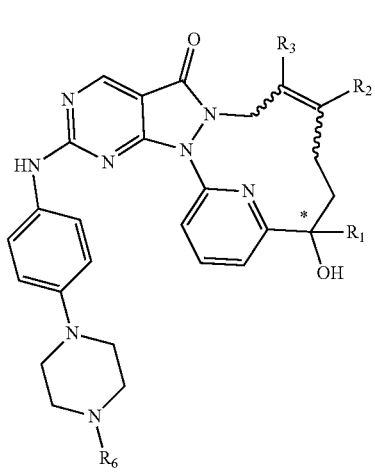
(II-A1)

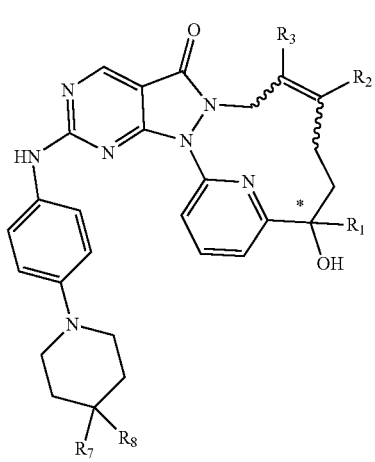
(II-A2)

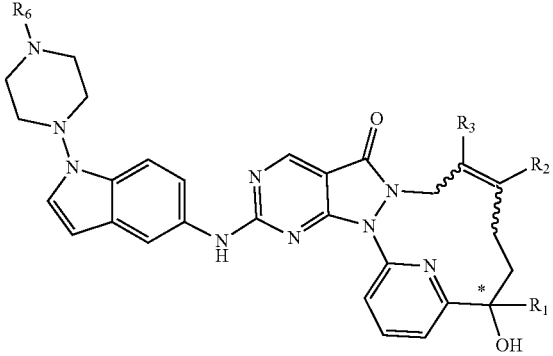
(III-AA1)

wherein, $R_1$ is selected from the group consisting of H and $C_{1-3}$ alkyl, wherein the $C_{1-3}$ alkyl is optionally substituted by 1, 2 or 3 $R_a$;

$R_2$ and $R_3$ are each independently selected from the group consisting of H, F, Cl, Br, I, OH, $NH_2$ and $C_{1-3}$ alkyl, wherein the $C_{1-3}$ alkyl is optionally substituted by 1, 2 or 3 $R_b$, and $R_2$ and $R_3$ are not H at the same time;

$R_a$ is each independently selected from the group consisting of F, Cl, Br, I, OH and $NH_2$;

$R_b$ is each independently selected from the group consisting of F, Cl, Br, I, OH and $NH_2$;

$R_6$ is each independently selected from the group consisting of H and $C_{1-3}$ alkyl, wherein the $C_{1-3}$ alkyl is optionally substituted by 1, 2 or 3 $R_e$;

$R_e$ is each independently selected from the group consisting of F, Cl, Br, I, OH and $NH_2$;

$R_7$ and $R_8$ are each independently selected from the group consisting of H, F, Cl, Br, I, OH, $NH_2$ and $C_{1-3}$ alkyl, wherein the $NH_2$ is optionally substituted by 1 or 2 $R_f$, and the $C_{1-3}$ alkyl is optionally substituted by 1, 2 or 3 $R_f$;

$R_f$ is each independently selected from the group consisting of F, Cl, Br, I, OH, $NH_2$ and $C_{1-3}$ alkyl;

the carbon atom with "*" is a chiral carbon atom, which is present in a form of a single enantiomer as (R) or (S) or in a form enriched with an enantiomer;

the "⌇" refers to (Z) stereoisomer, (E) stereoisomer or a mixture of two stereoisomers of the compound.

18. The compound according to claim 17, or a stereoisomer or a pharmaceutically acceptable salt thereof, wherein the compound has the structure of formula (II-1), (II-2) or (III-A1)

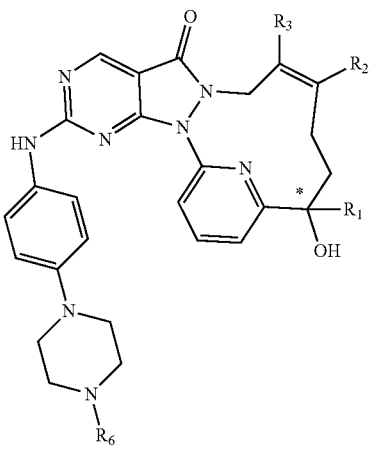

(II-1)

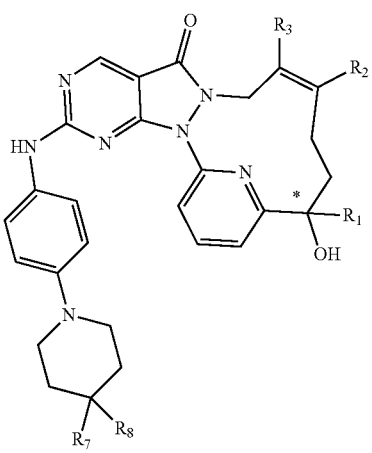

(II-2)

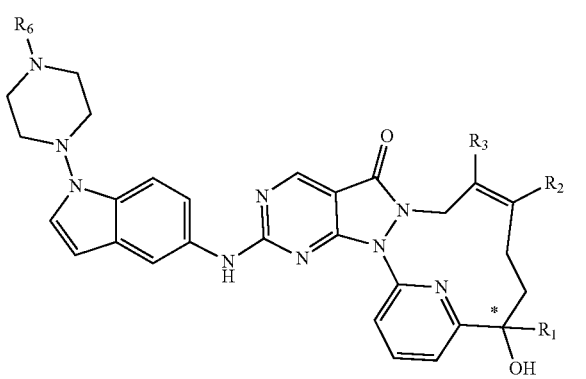

(III-A1)

wherein

R₁ is selected from the group consisting of H and $C_{1-3}$ alkyl, wherein the $C_{1-3}$ alkyl is optionally substituted by 1, 2 or 3 $R_a$;

R₂ and R₃ are each independently selected from the group consisting of H, F, Cl, Br, I, OH, $NH_2$ and $C_{1-3}$ alkyl, wherein the $C_{1-3}$ alkyl is optionally substituted by 1, 2 or 3 $R_b$, and R₂ and R₃ are not H at the same time;

$R_a$ is each independently selected from the group consisting of F, Cl, Br, I, OH and $NH_2$;

$R_b$ is each independently selected from the group consisting of F, Cl, Br, I, OH and $NH_2$;

$R_6$ is each independently selected from the group consisting of H and $C_{1-3}$ alkyl, wherein the $C_{1-3}$ alkyl is optionally substituted by 1, 2 or 3 $R_e$;

$R_e$ is each independently selected from the group consisting of F, Cl, Br, I, OH and $NH_2$;

R₇ and R₈ are each independently selected from the group consisting of H, F, Cl, Br, I, OH, $NH_2$ and $C_{1-3}$ alkyl, wherein the $NH_2$ is optionally substituted by 1 or 2 $R_f$, and the $C_{1-3}$ alkyl is optionally substituted by 1, 2 or 3 $R_f$;

$R_f$ is each independently selected from the group consisting of F, Cl, Br, I, OH, $NH_2$ and $C_{1-3}$ alkyl;

the carbon atom with "*" is a chiral carbon atom, which is present in a form of a single enantiomer as (R) or (S) or in a form enriched with an enantiomer.

19. The compound according to claim 1, or a stereoisomer or a pharmaceutically acceptable salt thereof, wherein the compound is selected from the group consisting of

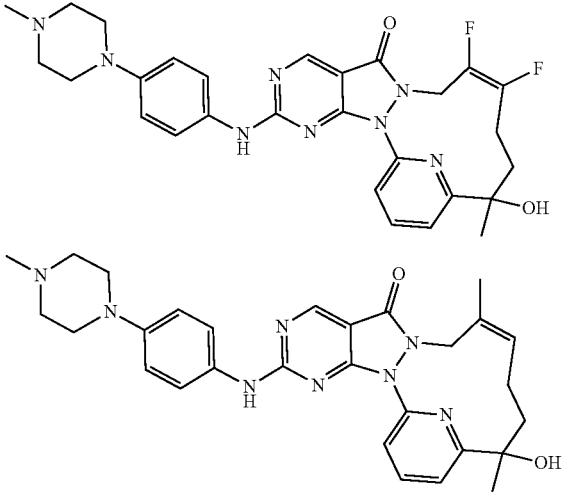

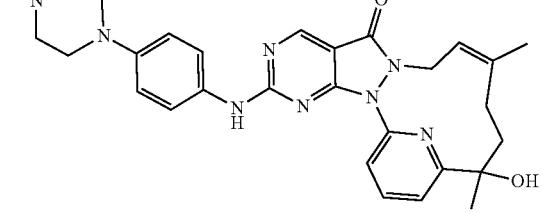

-continued
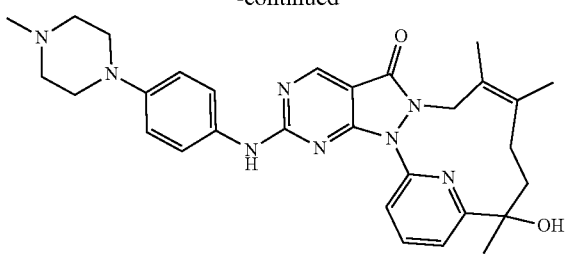
20. The compound according to claim 19, or a stereoisomer or a pharmaceutically acceptable salt thereof, wherein the compound is selected from the group consisting of
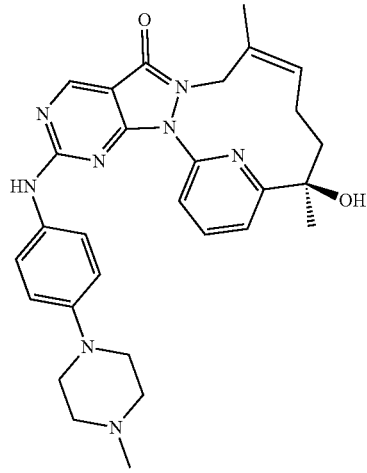
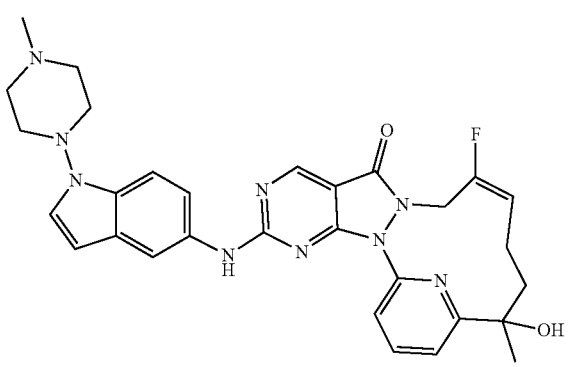
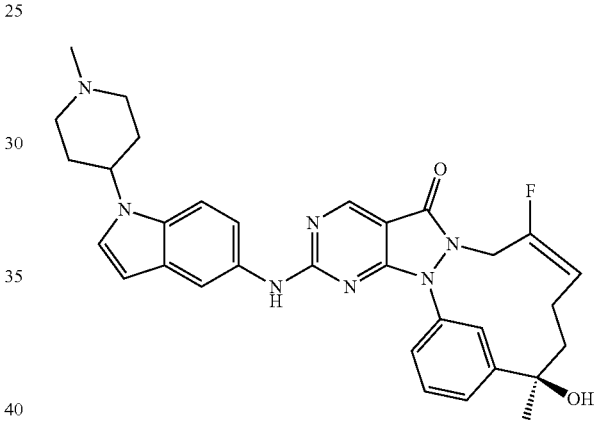
and
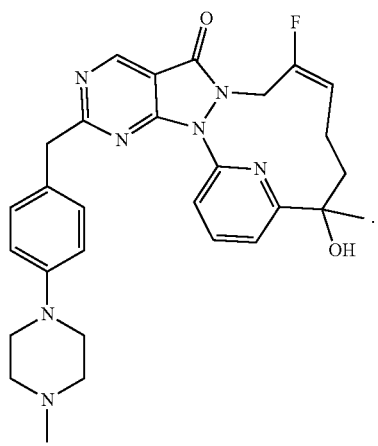
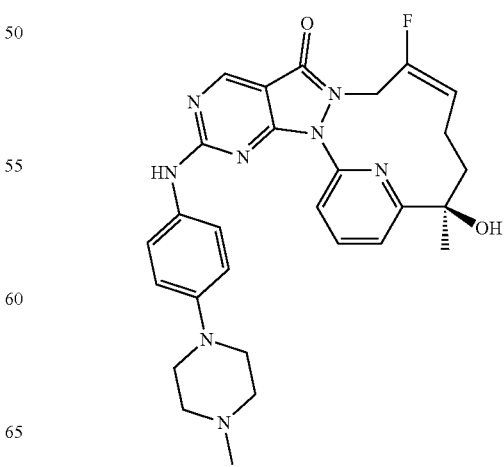

-continued
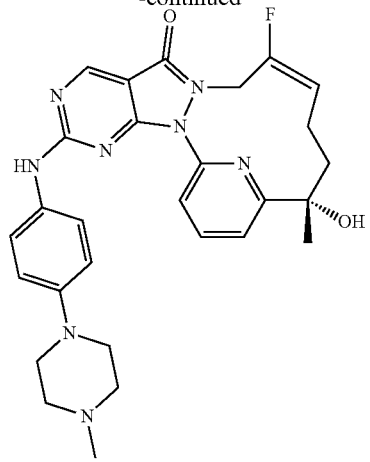
-continued
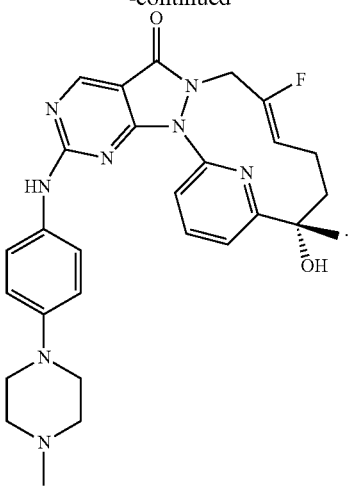
21. A method for treating pancreatic cancer, comprising administering the compound according to claim 1, or a stereoisomer or a pharmaceutically acceptable salt thereof to a subject in need thereof.
22. A pharmaceutical composition, comprising the compound according to claim 1, or a stereoisomer or a pharmaceutically acceptable salt thereof.
* * * * *

UNITED STATES PATENT AND TRADEMARK OFFICE
CERTIFICATE OF CORRECTION

PATENT NO. : 12,180,184 B2
APPLICATION NO. : 17/288707
DATED : December 31, 2024
INVENTOR(S) : Wenyuan Qian et al.

It is certified that error appears in the above-identified patent and that said Letters Patent is hereby corrected as shown below:

In the Claims

Claim 4, Column 54, Line 36:
"xN(R$_6$)—"
Should be replaced with:
"—N(R$_6$)—"

Claim 19, Column 61, Lines 50-65 Should read:

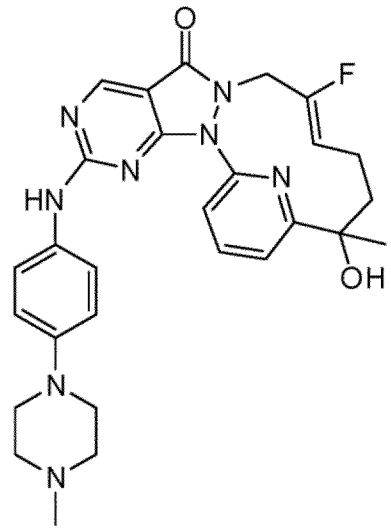

Signed and Sealed this
Twenty-ninth Day of April, 2025

Coke Morgan Stewart
*Acting Director of the United States Patent and Trademark Office*

CERTIFICATE OF CORRECTION (continued)
U.S. Pat. No. 12,180,184 B2

Claim 20, Column 62, Lines 25-40 Should read: